(12) United States Patent
Yoshida et al.

(10) Patent No.: US 7,534,370 B2
(45) Date of Patent: May 19, 2009

(54) POLYMERIZABLE LIQUID CRYSTAL COMPOSITION, OPTICAL ANISOTROPIC MATERIAL, OPTICAL ELEMENT AND OPTICAL HEAD DEVICE

(75) Inventors: Kara Yoshida, Koriyama (JP); Tomoki Gunjima, Chikushino (JP); Nobuhiko Takeshita, Koriyama (JP); Yuzuru Tanabe, Tokyo (JP); Hiroki Hotaka, Koriyama (JP); Hiromasa Sato, Koriyama (JP)

(73) Assignee: Asahi Glass Company, Limited, Tokyo (JP)

(*) Notice: Subject to any disclaimer, the term of this patent is extended or adjusted under 35 U.S.C. 154(b) by 0 days.

(21) Appl. No.: 11/872,267

(22) Filed: Oct. 15, 2007

(65) Prior Publication Data
US 2008/0048149 A1   Feb. 28, 2008

Related U.S. Application Data

(63) Continuation of application No. PCT/JP2006/307779, filed on Apr. 12, 2006.

(30) Foreign Application Priority Data

Apr. 13, 2005 (JP) ............... 2005-115886
Dec. 16, 2005 (JP) ............... 2005-362891

(51) Int. Cl.
C09K 19/32 (2006.01)
C09K 19/38 (2006.01)
C09K 19/30 (2006.01)
C09K 19/20 (2006.01)
C07C 69/75 (2006.01)
C07C 69/753 (2006.01)
G02B 5/30 (2006.01)

(52) U.S. Cl. .............. 252/299.62; 252/299.63; 428/1.1; 428/1.3; 428/1.31; 560/80; 560/100

(58) Field of Classification Search ............... 428/1.1, 428/1.3, 1.31; 252/299.01, 299.62, 299.64, 252/299.65, 299.67, 299.63; 560/80, 100
See application file for complete search history.

(56) References Cited

U.S. PATENT DOCUMENTS 5,851,427 A * 12/1998 Kelly .................... 252/299.62
6,118,586 A *  9/2000 Tanabe et al. ............ 359/566
6,271,966 B1 *  8/2001 Tanabe et al. ............ 359/566

FOREIGN PATENT DOCUMENTS

| JP | 7-82183 | 3/1995 |
|---|---|---|
| JP | 8-245520 | 9/1996 |
| JP | 10-68816 | 3/1998 |
| JP | 2001-4986 | 1/2001 |
| JP | 2001-220583 | 8/2001 |
| JP | 2002-267838 | 9/2002 |
| JP | 2003-27060 | 1/2003 |
| JP | 2003-160540 | 6/2003 |
| JP | 2004-285340 | 10/2004 |

OTHER PUBLICATIONS

English translation by computer for JP 2003-27060, http://www4.ipdl.inpit.go.jp/Tokujitu/PAJdetail.ipdl?N0000=60&N0120=01&N2001=2&N3001=2003-027060.*

* cited by examiner

*Primary Examiner*—Shean C Wu
(74) *Attorney, Agent, or Firm*—Oblon, Spivak, McClelland, Maier & Neustadt, P.C.

(57) ABSTRACT

To provide optical elements such as a phase plate suitably used in a broadband range and a polarizing diffraction element excellent in diffraction efficiency, a polymerizable liquid crystal composition to be used for them, and an optical head device using them.

A polymerizable liquid crystal composition containing a polymerizable compound having a mesogen structure comprising the following condensed benzene ring group (A) and the following 6-membered cyclic group (B) bonded to at least one bond in the group (A) directly or via a connecting group —OCO— or —COO—, and a monovalent terminal group bonded to each of both terminals of the mesogen structure, at least one of the terminal groups being a monovalent organic group having a polymerizable moiety:
condensed benzene ring group (A): a naphthalenediyl group having bonds at 1-position and at 4- or 5-position, or an anthracenediyl group having bonds at 1- or 9-position and at 4-, 5- or 10-position;
6-membered cyclic group (B): a 1,4-phenylene group, a trans-1,4-cyclohexylene group or a bivalent group having at least two groups selected from these groups bonded directly or via a connecting group.

14 Claims, 5 Drawing Sheets

POLYMERIZABLE LIQUID CRYSTAL COMPOSITION, OPTICAL ANISOTROPIC MATERIAL, OPTICAL ELEMENT AND OPTICAL HEAD DEVICE

TECHNICAL FIELD

The present invention relates to a polymerizable compound useful for preparation of an optical anisotropic material capable of controlling wavelength dispersion of the refractive index anisotropy, a polymerizable liquid crystal composition containing such a polymerizable compound, an optical element using it and an optical head device.

BACKGROUND ART

Liquid crystal molecules having polymerizable functional groups have both characteristics as a polymerizable monomer and characteristics as a liquid crystal. Accordingly, if they are polymerized in a state where they are aligned, it is possible to obtain a polymer with fixed alignment, i.e. an optical anisotropic material. The optical anisotropic material thus obtained has an optical anisotropy based on the refractive index anisotropy derived from a mesogen skeleton and is applied to e.g. an optical element such as a diffraction element or a phase plate by the use of such a characteristic.

A phase plate using a polymer liquid crystal is known to have low temperature dependence of phase difference (or retardation) as compared with a phase plate using a low molecular weight liquid crystal.

As such a phase plate, for example, Patent Document 1 discloses "a phase plate comprising a quarter wave plate to create a quarter wave phase shift of birefringent light and a half wave plate to create a half wave phase shift of birefringent light in a state where their optical axes intersect with each other", and discloses that the phase plate is prepared by laminating a quarter wave plate and a half wave plate obtained by stretching a polymer film (particularly polycarbonate). However, for the phase plate disclosed in Patent Document 1, a plurality of wave plates have to be laminated, and complicated production process is required.

Further, Patent Document 2 discloses "a phase difference film having a liquid crystal layer containing a compound having two or more kinds of mesogen groups and a rod-like liquid crystal compound, wherein the rod-like liquid crystal compound is homogenously aligned, and at least one kind of the mesogen group of the compound containing mesogen groups is aligned in a direction of from 45 to 90 degree with the direction of the optical axis of the rod-like liquid crystal compound in a plane of a film", and discloses that a phase plate utilizing wavelength dispersion of a phase difference can be produced by such a film. However, since two different materials of the compound containing two or more kinds of mesogen groups and the rod-like liquid crystal compound are required, the degree of freedom in design is restricted, such that various combinations must be considered to meet desired properties, and materials appropriate for the combination must be selected and obtained.

Further, Patent Document 3 discloses "a four-membered cyclic compound represented by the following formula (I):

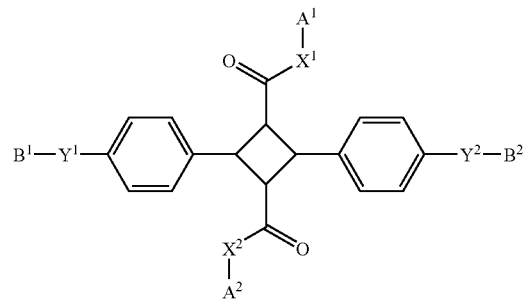

wherein each of $X^1$ and $X^2$ which are independent of each other, is an oxygen atom, a sulfur atom or the like, each of $Y^1$ and $Y^2$ which are independent of each other, is a single bond, an oxygen atom, or the like, each of $B^1$ and $B^2$ which are independent of each other, is a $C_{1-20}$ aliphatic group which may have a substituent, or the like, each of two benzene rings directly bonded to the cyclobutane ring may have a substituent on the ring, and each of $A_1$ and $A_2$ which are independent of each other, is a group represented by the following formula (II):

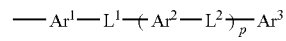

wherein each of $Ar^1$, $Ar^2$ and $Ar^3$ which are independent of each other, is a $C_{5-14}$ cyclic group, or the like, each of $L^1$ and $L^2$ which are independent of each other, is a single bond or a bivalent connecting group, and p is an integer of from 0 to 2, provided that when p is 2, two $Ar^2$'s and two $L^2$'s may be the same or different", and discloses that a phase plate which controls wavelength dispersion of a phase difference can be produced by such a compound.

Further, Patent Document 4 which discloses an invention focusing on a tolan liquid crystal to be used for a liquid crystal element for high resolution polymer-dispersed type liquid crystal display, discloses, as a polymerizable liquid crystal compound, a liquid crystal compound containing —C≡C— as a connecting group. As one of many examples, a polymerizable liquid crystal compound represented by the following formula (III) having a —C≡C— connecting group between a naphthalene-1,4-diyl group and a 1,4-phenylene group, is disclosed in paragraph number 0083:

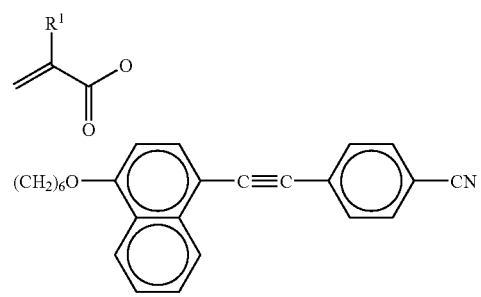

wherein $R^1$ is a hydrogen atom, an alkyl group, a phenyl group or a halogen.

Patent Document 1: JP-A-10-68816

Patent Document 2: JP-A-2002-267838
Patent Document 3: JP-A-2003-160540
Patent Document 4: JP-A-7-082183

DISCLOSURE OF THE INVENTION

Object to be Accomplished by the Invention

However, it was found that even with a phase plate using the four-membered cyclic compound disclosed in Patent Document 3, the wavelength dispersion properties are not sufficiently improved in some cases. Further, there is worry that the chemically unstable cyclobutane ring decomposes by light or heat during preparation of a phase plate or depending upon conditions during use, and the wavelength dispersion properties deteriorate.

Further, the compound disclosed in Patent Document 4 is to increase the refractive index anisotropy by prolonging the conjugation. In such a case, it is well known that the wavelength dependence of the refractive index anisotropy increases. Therefore, a wave plate using it tends to have poor wavelength dispersion properties.

It has not yet been studied to decrease the wavelength dependence of the refractive index anisotropy in control of the wavelength dispersion, and particularly, a liquid crystal material of which the refractive index anisotropy increases as the wavelength of light to be used increases, is strongly desired since it is excellent in use in a broadband range, but a material with wide degree of freedom, capable of being used stably, has not been found yet.

The present invention is to solve the above various problems, and its object is to provide optical elements such as a phase plate suitably used in a broadband range and a polarizing diffraction element excellent in diffraction efficiency, a polymerizable liquid crystal composition to be used for them, and an optical head device using such an optical element.

Means to Accomplish the Object

The present inventors have conducted extensive studies to accomplish the above object and as a result, found that an optical anisotropic material obtained by polymerizing a polymerizable liquid crystal composition containing a polymerizable compound having a predetermined mesogen structure is capable of controlling the wavelength dispersion of the refractive index anisotropy in its molecule and accomplished the present invention.

Namely, the present invention provides the following (I) to (XIII).

(I) A polymerizable liquid crystal composition containing a polymerizable compound (hereinafter sometimes referred to a "polymerizable compound (3)") having a mesogen structure comprising the following condensed benzene ring group (A) and the following 6-membered cyclic group (B) bonded to at least one bond in the group (A) directly or via a connecting group —OCO— or —COO—, and a monovalent terminal group bonded to each of both terminals of the mesogen structure, at least one of the terminal groups being a monovalent organic group having a polymerizable moiety:

condensed benzene ring group (A): a naphthalenediyl group having bonds at 1-position and at 4- or 5-position, or an anthracenediyl group having bonds at 1- or 9-position and at 4-, 5- or 10-position;

6-membered cyclic group (B): a 1,4-phenylene group, a trans-1,4-cyclohexylene group or a bivalent group having at least two groups selected from these groups bonded directly or via a connecting group.

(II) The polymerizable liquid crystal composition according to the above (I), which contains a polymerizable compound represented by the following formula (1):

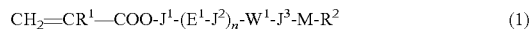

$$CH_2=CR^1-COO-J^1-(E^1-J^2)_n-W^1-J^3-M-R^2 \qquad (1)$$

wherein $R^1$, $R^2$, n, $J^1$, $J^2$, $J^3$, $E^1$, $W^1$ and M are as follows:

$R^1$: a hydrogen atom or a methyl group, $R^2$: a $C_{2-8}$ alkyl group, n: 0 or 1, $J^1$: a single bond, —$(CH_2)_a$— or —$(CH_2)_bO$— (wherein each of "a" and "b" which are independent of each other, is an integer of from 2 to 8), $J^2$, $J^3$: each independently a single bond, —OCO— or —COO—, $E^1$: a 1,4-phenylene group or a trans-1,4-cyclohexylene group, provided that a hydrogen atom in such a group may be substituted by a chlorine atom, a fluorine atom, a methyl group or a cyano group, $W^1$: a naphthalene-1,4-diyl group, a naphthalene-1,5-diyl group, an anthracene-1,4-diyl group, an anthracene-1,5-diyl group, an anthracene-1,10-diyl group, an anthracene-4,9-diyl group, an anthracene-5,9-diyl group or an anthracene-9,10-diyl group, provided that a hydrogen atom in such a group may be substituted by a chlorine atom, a fluorine atom, a methyl group or a cyano group, and M: a group selected from groups represented by the following formulae (a) to (f):

(a)

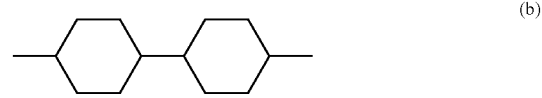

(b)

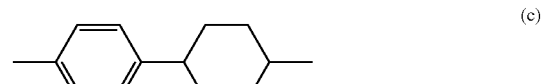

(c)

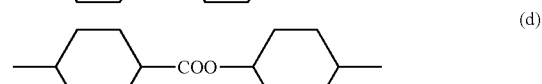

(d)

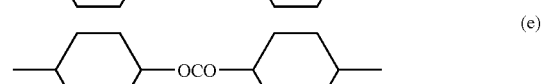

(e)

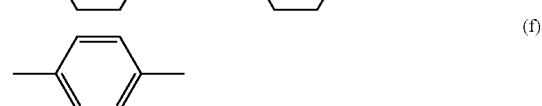

(f)

(III) The polymerizable liquid crystal composition according to the above (II), which contains a polymerizable compound wherein M is a group selected from groups represented by the following formulae (a) to (e):

(a)

-continued

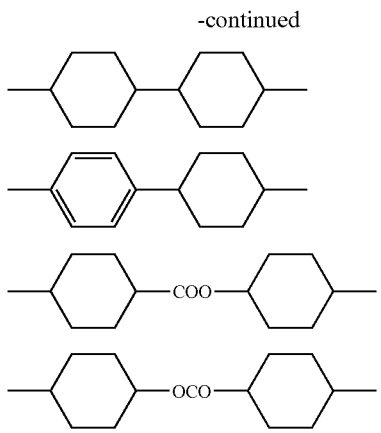
(b)
(c)
(d)
(e)

(IV) The polymerizable liquid crystal composition according to the above (III), which contains a polymerizable compound wherein M is a trans-1,4-cyclohexylene group or a trans, trans-4,4'-bicyclohexylene group.

(V) The polymerizable liquid crystal composition according to the above (I), which contains a polymerizable compound represented by the following formula (2):

$$CH_2=CR^3-COO-J^4-E^2-COO-W^2-OCO-E^3-J^5-OCO-CR^3=CH_2 \quad (2)$$

wherein $R^3$, $J^4$, $J^5$, $E^2$, $E^3$, and $W^2$ are as follows:

$R^3$: a hydrogen atom or a methyl group, $J^4$: $-(CH_2)_tO-$ or $-(CH_2)_uO-CO-$ (wherein each of "t" and "u" which are independent of each other, is an integer of from 2 to 6), $J^5$: $-O(CH_2)_c-$ or $-COO-(CH_2)_d-$ (wherein each of "c" and "d" which are independent of each other, is an integer of from 2 to 6)

$E^2$, $E^3$: each independently a 1,4-phenylene group or a trans-1,4-cyclohexylene group, provided that a hydrogen atom in such a group may be substituted by a chlorine atom, a fluorine atom, a methyl group or a cyano group, and $W^2$: a naphthalene-1,4-diyl group, a naphthalene-1,5-diyl group, an anthracene-1,4-diyl group, an anthracene-1,5-diyl group, an anthracene-1,10-diyl group, an anthracene-4,9-diyl group, an anthracene-5,9-diyl group or an anthracene-9,10-diyl group, provided that a hydrogen atom in such a group may be substituted by a chlorine atom, a fluorine atom, a methyl group or a cyano group.

(VI) The polymerizable liquid crystal composition according to any one of the above (I) to (V), wherein the content of the polymerizable compound is at least 10 mass % based on the polymerizable liquid crystal composition.

(VII) An optical anisotropic material obtained by polymerizing the polymerizable liquid crystal composition as defined in any one of the above (I) to (V).

(VIII) The optical anisotropic material according to the above (VII), which is optically uniaxial and of which the value of refractive index anisotropy Δn which is a difference between the ordinary refractive index $n_o$ and the extraordinary refractive index $n_e$ increases as the wavelength of light to be used increases.

(IX) An optical element to control polarization state and/or phase state of light to be used, formed by using the optical anisotropic material as defined in the above (VII) or (VIII).

(X) A phase plate, formed by using the optical anisotropic material as defined in the above (VII) or (VIII).

(XI) A polarizing diffraction element having a diffraction grating region to diffract incident light, wherein the diffraction grating region comprises a first member made of a first material and a second member made of a second material, the first member and the second member differ from each other in the refractive index to at least one polarized light, and the first member and the second member are disposed alternately to be in contact with each other; and the first material is the optical anisotropic material as defined in the above (VII) or (VIII).

(XII) An optical head device comprising a semiconductor laser, an objective lens and a photodetector, and a phase plate and/or a polarizing diffraction element disposed between the objective lens and the photodetector, wherein the phase plate is the phase plate as defined in the above (X), and/or the polarizing diffraction element is the polarizing diffraction element as defined in the above (XI).

(XIII) A polymerizable compound represented by the following formula (1) or (2):

$$CH_2=CR^1-COO-J^1-(E^1-J^2)_n-W^1-J^3-M-R^2 \quad (1)$$

$$CH_2=CR^3-COO-J^4-E^2-COO-W^2-OCO-E^3-J^5-OCO-CR^3=CH_2 \quad (2)$$

wherein $R^1$, $R^2$, $R^3$, n, $J^1$, $J^2$, $J^3$, $J^4$, $J^5$, $E^1$, $E^2$, $E^3$, $W^1$, $W^2$ and M are as follows:

$R^1$ and $R^3$: each independently a hydrogen atom or a methyl group, $R^2$: a $C_{2-8}$ alkyl group, n: 0 or 1, $J^1$: a single bond, $-(CH_2)_a-$ or $-(CH_2)_bO-$ (wherein each of "a" and "b" which are independent of each other, is an integer of from 2 to 8), $J^2$; $J^3$: each independently a single bond, $-OCO-$ or $-COO-$, $J^4$: $-(CH_2)_tO-$ or $-(CH_2)_uO-CO-$ (wherein each of "t" and "u" which are independent of each other, is an integer of from 2 to 6), is $J^5$: $-O(CH_2)_c-$ or $-COO-(CH_2)_d-$ (wherein each of "c" and "d" which are independent of each other, is an integer of from 2 to 6)

$E^1$, $E^2$, $E^3$: each independently a 1,4-phenylene group or a trans-1,4-cyclohexylene group, provided that a hydrogen atom in such a group may be substituted by a chlorine atom, a fluorine atom, a methyl group or a cyano group, $W^1$, $W^2$: each independently a naphthalene-1,4-diyl group, a naphthalene-1,5-diyl group, an anthracene-1,4-diyl group, an anthracene-1,5-diyl group, an anthracene-1,10-diyl group, an anthracene-4,9-diyl group, an anthracene-5,9-diyl group or an anthracene-9,10-diyl group, provided that a hydrogen atom in such a group may be substituted by a chlorine atom, a fluorine atom, a methyl group or a cyano group, and M: a group selected from groups represented by the following formulae (a) to (f):

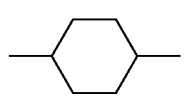
(a)

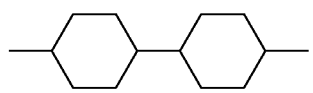
(b)

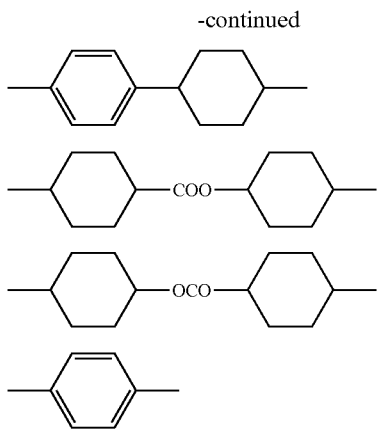

(c)

(d)

(e)

(f)

EFFECTS OF THE INVENTION

According to the present invention, a polymerizable compound useful for adjustment of the wavelength dispersion of the refractive index anisotropy, and a polymerizable liquid crystal composition containing such a polymerizable compound can be obtained. By use of the polymerizable liquid crystal composition, the wavelength dependence of a phase difference can be reduced in a certain wavelength region, and a phase plate particularly suitably used in a broadband range, and a polarizing diffraction element excellent in diffraction efficiency, can be obtained.

MEANINGS OF SYMBOLS

Figure 1:
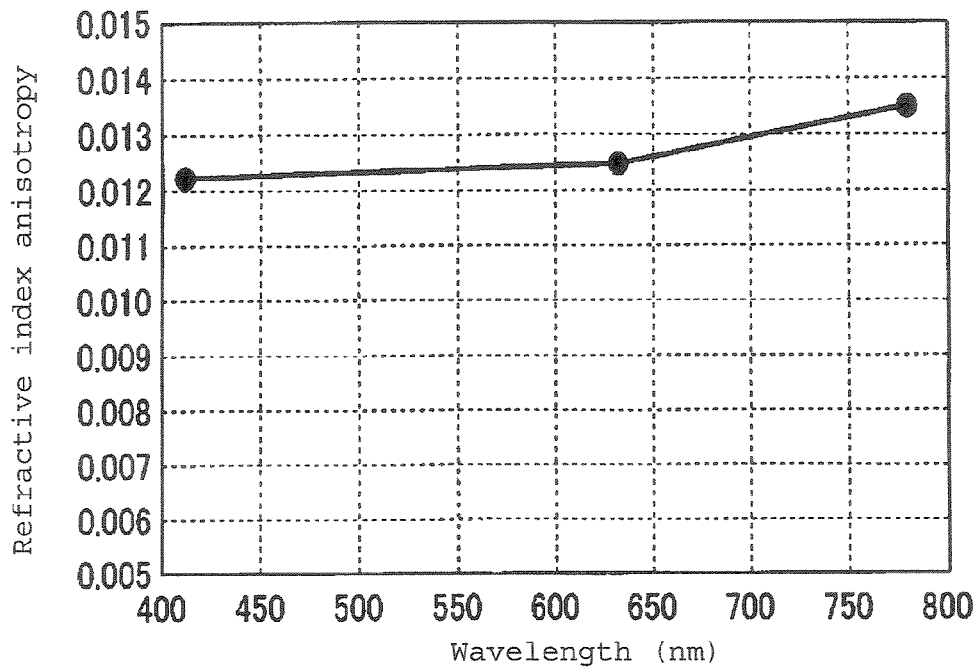
FIG. 1 is a graph illustrating the wavelength dependence of the refractive index anisotropy of a phase plate A obtained in Example 7.

301, 302: Semiconductor laser
304, 305: Photodetector
308: Light-combiner prism
310: Collimater lens
311: Polarizing diffraction element
312: Broadband phase plate
313: Objective lens
314: Actuator
315: Optical disk

BEST MODE FOR CARRYING OUT THE INVENTION

The polymerizable liquid crystal composition of the present invention is a polymerizable liquid crystal composition containing a polymerizable compound having a mesogen structure comprising the following condensed benzene ring group (A) and the following 6-membered cyclic group (B) bonded to at least one bond in the group (A) directly or via a connecting group —OCO— or —COO—, and a monovalent terminal group bonded to each of both terminals of the mesogen structure, at least one of the terminal groups being a monovalent organic group having a polymerizable moiety:

condensed benzene ring group (A): a naphthalenediyl group having bonds at 1-position and at 4- or 5-position, or an anthracenediyl group having bonds at 1- or 9-position and at 4-, 5- or 10-position;

6-membered cyclic group (B): a 1,4-phenylene group, a trans-1,4-cyclohexylene group or a bivalent group having at least two groups selected from these groups bonded directly or via a connecting group.

The above condensed benzene ring group (A) is a bivalent group having such a structure that at least two benzene rings are linearly condensed, and two bonds are present at right angles to the direction of condensation of the benzene rings and opposite to each other. The number of benzene rings condensed is 2 or 3, particularly preferably 2. That is, the condensed benzene ring group (A) is a naphthalenediyl group having bonds at 1-position and at 4- or 5-position, or an anthracenediyl group having bonds at 1- or 9-position and at 4-, 5- or 10-position, particularly preferably such a naphthalenediyl group.

The 6-membered cyclic group (B) is a 1,4-phenylene group, a trans-1,4-cyclohexylene group or a bivalent group having at least two groups selected from these groups bonded directly or via a connecting group (C). The connecting group (C) is —OCO— or —COO—.

The 6-membered cyclic group (B) is preferably, for example, a 1,4-phenylene group, a trans-1,4-cyclohexylene group or the following groups (B1) to (B4), more preferably a trans-1,4-cyclohexylene group or the following groups (B1) to (B4), and particularly preferably a trans-1,4-cyclohexylene group or the following group (B1), with which the effect of optical anisotropy of the condensed benzene ring group (A) can sufficiently be exhibited.

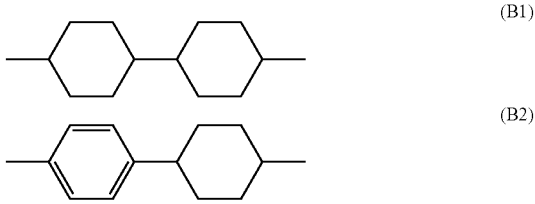

-continued
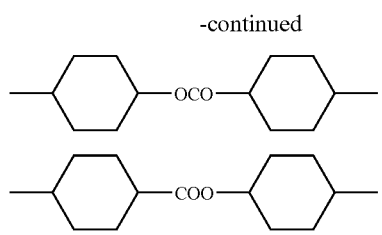
(B3)
(B4)
The above polymerizable compound (3) has a mesogen structure comprising the condensed benzene ring group (A) and the 6-membered cyclic group (B) bonded to at least one bond in the group (A) directly or via a connecting group (C).
The connecting group (C) is —OCO— or —COO—.
As the mesogen structure, for example, the following structures are preferred.
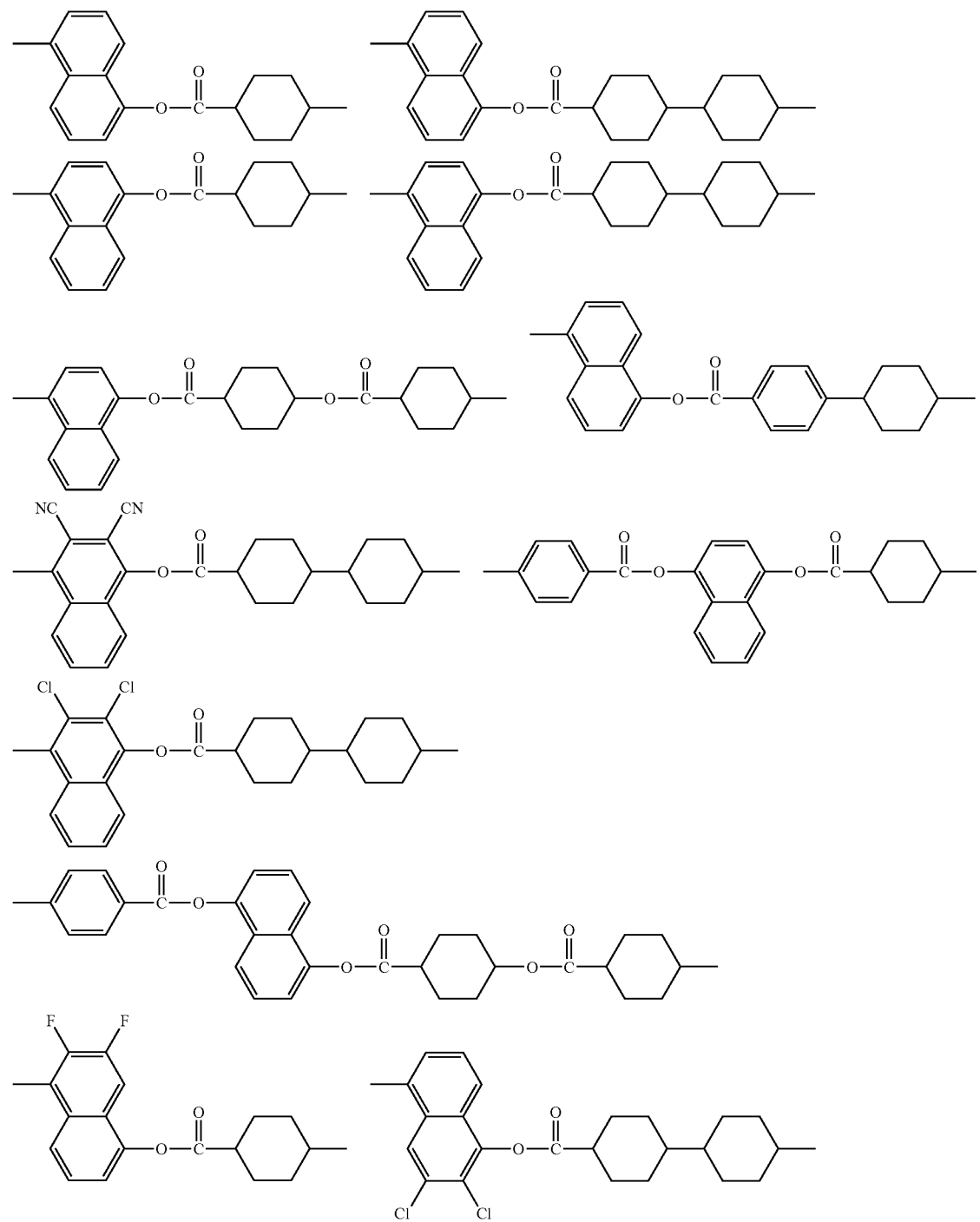

-continued

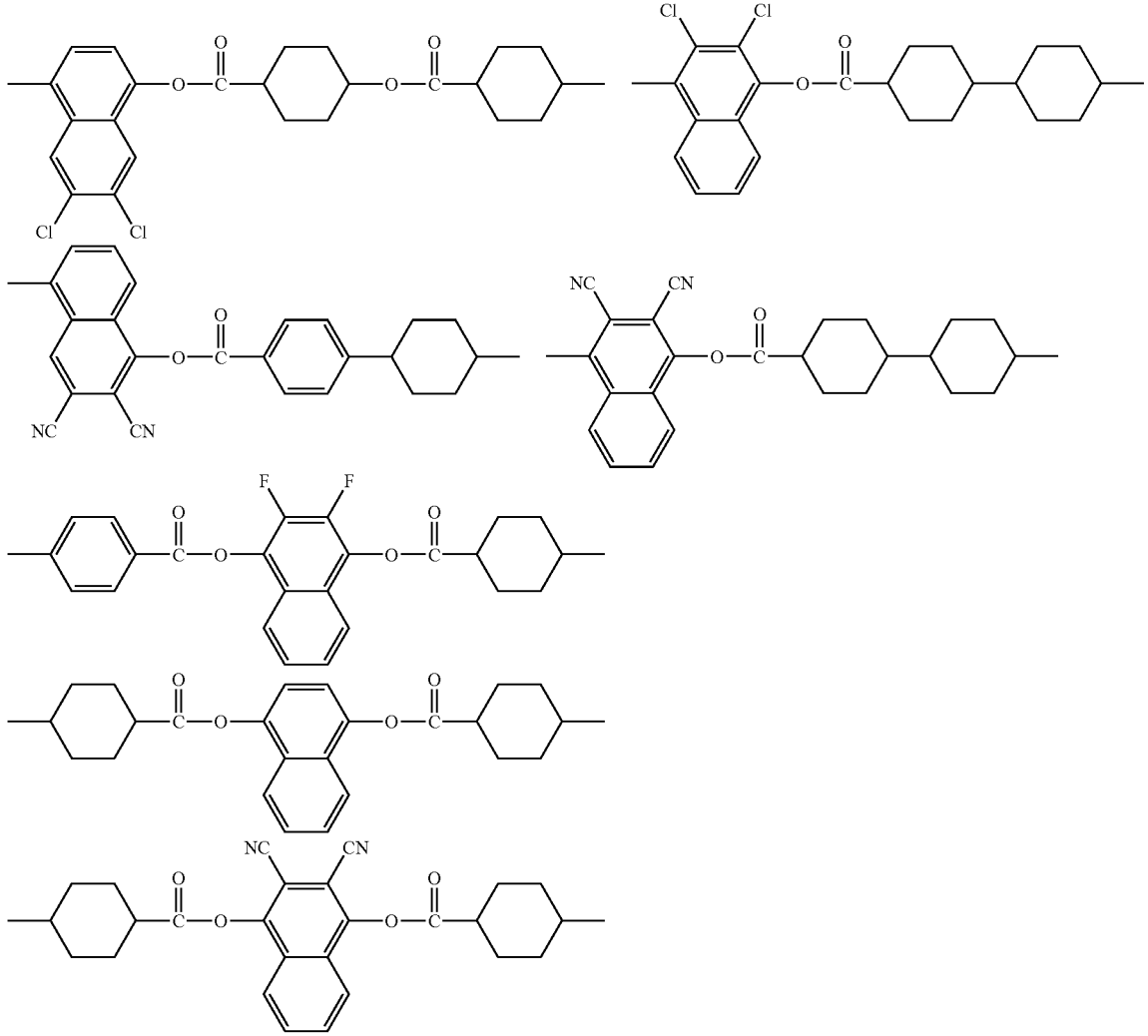

To each of both terminals of the above mesogen structures, a monovalent terminal group is bonded.

The terminal group may, for example, be preferably an alkyl group, an alkoxy group, a polymerizable functional group, or a monovalent organic group having a polymerizable moiety, particularly preferably an alkyl group, a polymerizable functional group or a monovalent organic group having a polymerizable moiety. Further, at least one of the terminal groups is a polymerizable functional group or a monovalent organic group having a polymerizable moiety.

In a case where the terminal group is an alkyl group, preferred is a $C_{2-8}$ linear alkyl group, particularly preferably a $C_{2-6}$ linear alkyl group.

Further, in a case where the terminal group is an alkoxy group, preferred is a $C_{2-8}$ linear alkoxy group, particularly preferred is a $C_{2-6}$ linear alkoxy group.

Further, in a case where the terminal group is a polymerizable functional group, preferred is an acryloyl group or a methacryloyl group, and particularly preferred is an acryloyl group. In a case where the terminal group is a monovalent organic group having a polymerizable moiety, preferred is an organic group having a $CH_2$=$CH$—$COO$— moiety or a $CH_2$=$C(CH_3)$—$COO$— moiety, and particularly preferred is an organic group having a $CH_2$=$CH$—$COO$— moiety.

As the monovalent organic group having a polymerizable moiety, for example, the following groups are preferred:
$CH_2$=$CH$—$COO$—$(CH_2)_2$—$O$—, $CH_2$=$CH$—$COO$—$(CH_2)_3$—$O$—, $CH_2$=$CH$—$COO$—$(CH_2)_4$—$O$—, $CH_2$=$CH$—$COO$—$(CH_2)_5$—$O$—, $CH_2$=$CH$—$COO$—$(CH_2)_4$—$OCO$—.

Further, in a case where the number of the 6-membered cyclic group (B) bonded to the condensed benzene ring group (A) is 1, to the bond to which no 6-membered cyclic group (B) is bonded, a polymerizable functional group or a monovalent organic group having a polymerizable moiety is preferably bonded.

In the present invention, by using such a polymerizable compound (3), favorable wavelength dispersion properties of an optical anisotropic material to be obtained by using the polymerizable compound (3) will be obtained.

Another polymerizable liquid crystal composition of the present invention is a polymerizable liquid crystal composition containing at least two types of a polymerizable compound (1) represented by the following formula (1) and/or a polymerizable compound (2) represented by the following formula (2), of which adjustment of the wavelength dispersion of the refractive index anisotropy is made easy depending upon the purpose of use in a broadband range:

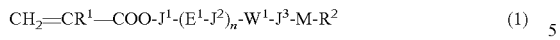
(1)

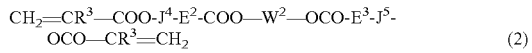
(2)

In the present invention, the polymerizable compound (1) and the polymerizable compound (2) may be a liquid crystalline compound or a non-liquid crystalline compound, so long as the polymerizable liquid crystal composition obtained by using such a polymerizable compound exhibits nematic liquid crystallinity. However, they are preferably a liquid crystalline compound, with which the obtained polymerizable liquid crystal composition tends to exhibit liquid crystallinity and the degree of freedom at the time of preparation of the composition will be high.

In the above formula (1), $R^1$ is preferably a hydrogen atom. When $R^1$ is a hydrogen atom, there is such an advantage that the polymerization rate is high when the after-mentioned polymerization reaction is carried out to obtain an optical anisotropic material.

The structure of the $C_{2-8}$ alkyl group as $R^2$ may be a linear structure or a branched structure, preferably a linear structure. The number of carbon atoms in $R^2$ is preferably from 2 to 6, so that the polymerizable compound (1) favorably exhibits nematic phase.

$J^1$ is preferably a single bond, whereby when an optical anisotropic material is obtained by polymerization reaction, excellent wavelength dispersion properties will be obtained. When $J^1$ is —$(CH_2)_a$— or —$(CH_2)_b$O— each of "a" and "b" which are independent of each other, is an integer of from 2 to 8, preferably an integer of from 2 to 5, particularly preferably an integer of from 2 to 4. Each of $J^2$ and $J^3$ is preferably —OCO—. When each of $J^2$ and $J^3$ is —OCO—, the crystal-nematic phase transition point of the polymerizable compound (1) will not be too high, whereby the compound will easily be handled.

$E^1$ is a 1,4-phenylene group or a trans-1,4-cyclohexylene group. These groups may be a non-substituted group or may be a group having a hydrogen atom in the above group substituted by a chlorine atom, a fluorine atom, a methyl group or a cyano group. $E^1$ is preferably a non-substituted group with a view to obtaining favorable liquid crystallinity of the polymerizable compound (1), and particularly preferably a non-substituted trans-1,4-cyclohexylene group from the following viewpoint. Namely, $W^1$ is originally a group with great optical anisotropy, but the optical anisotropy of $W^1$ decreases in some cases by the presence of $E^1$. Therefore, the optical anisotropy of $E^1$ should be small so as to effectively utilize the effect of the optical anisotropy of $W^1$, and accordingly it is considered that a trans-1,4-cyclohexylene group is more preferred to a 1,4-phenylene group with great optical anisotropy.

$W^1$ is preferably a naphthalene-1,4-diyl group or a naphthalene-1,5-diyl group. Such a group may be a non-substituted group or a group having a hydrogen atom in the above group substituted by a chlorine atom, a fluorine atom, a methyl group or a cyano group. $W^1$ is preferably the following groups (60a) to (60c) (in the formulae, X is a chlorine atom, a fluorine atom or a cyano group) with a view to increasing the wavelength dispersion properties of the optical anisotropic material. The effect of increasing the wavelength dispersion properties of the optical anisotropic material is high when X is a cyano group, then a chlorine atom and then a fluorine atom, but the material is properly selected considering the crystal-nematic phase transition point of the polymerizable compound (1).

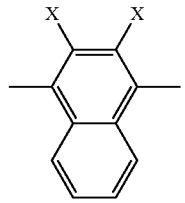
(60a)

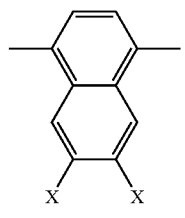
(60b)

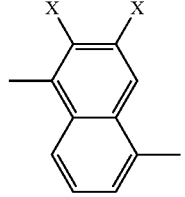
(60c)

M is a group selected from groups represented by the following formulae (a) to (f), and preferably a group represented by the following formula (a) or (b) with a view to effectively utilizing the effect of the optical anisotropy of $W^1$.

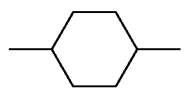
(a)

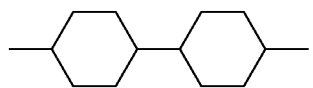
(b)

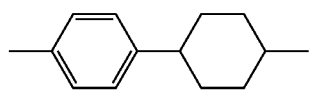
(c)

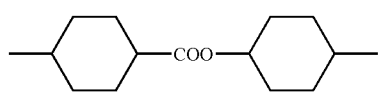
(d)

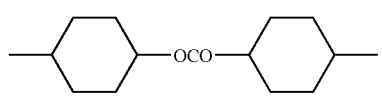
(e)

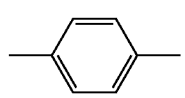
(f)

As the polymerizable compound (1), for example, the following compounds are preferred, and the following compounds (1A) to (1C), (1D), (1L), (1N) to (1Q), (1U), (1V) and (1W) are particularly preferred.

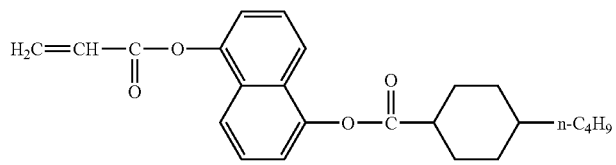 (1A)
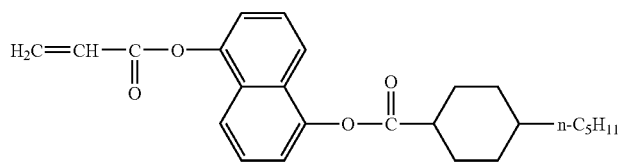 (1B)
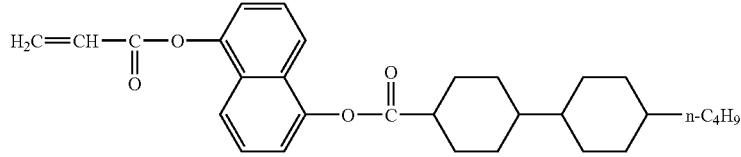 (1C)
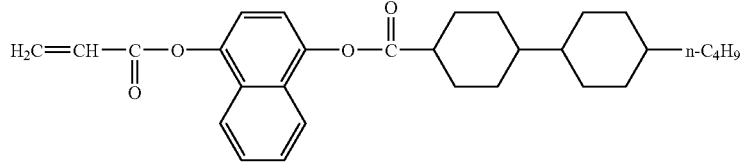 (1D)
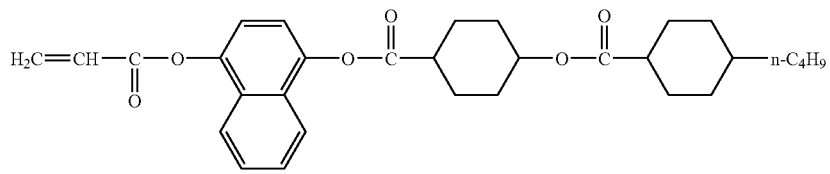 (1E)
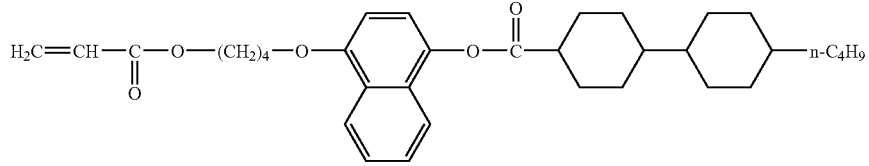 (1F)
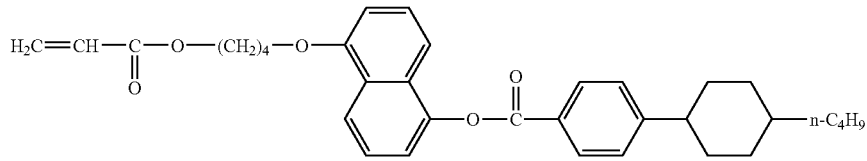 (1G)
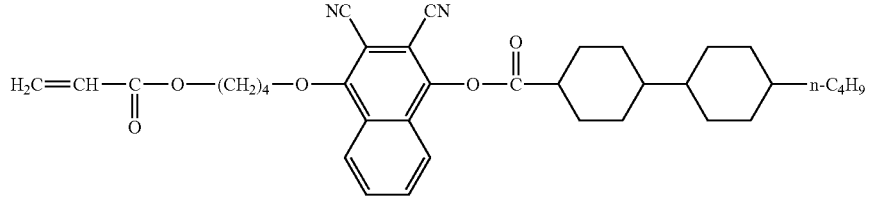 (1H)
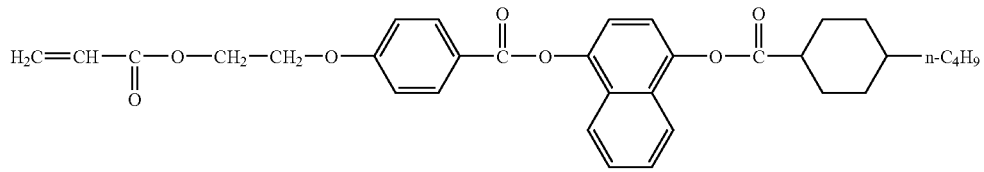 (1J)

-continued
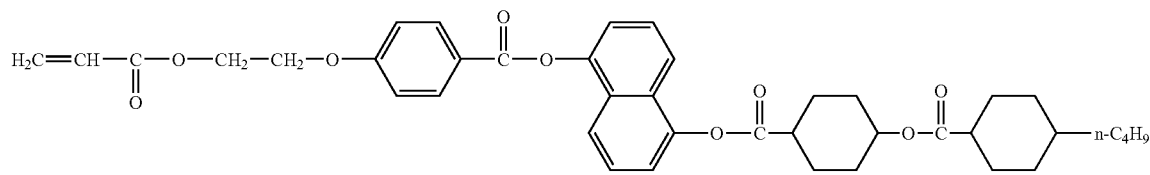
(1K)
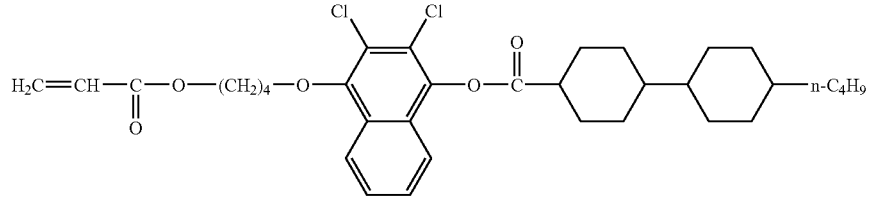
(1L)
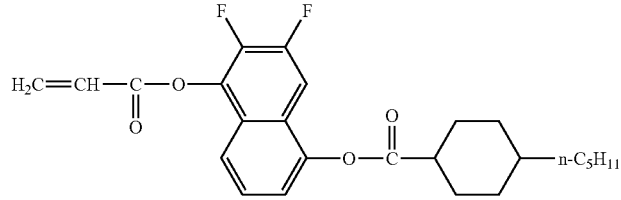
(1M)
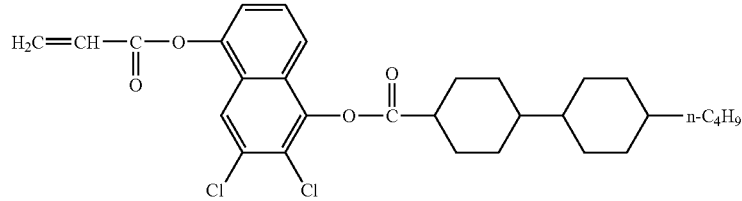
(1N)
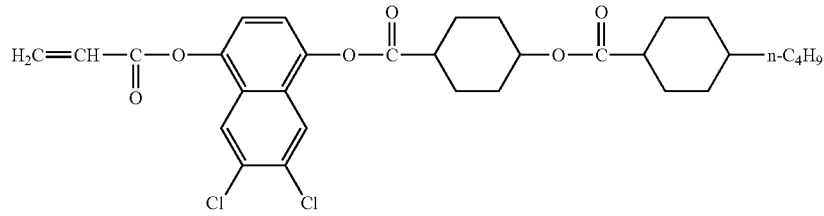
(1P)
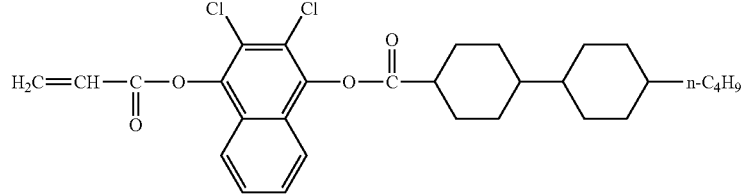
(1Q)
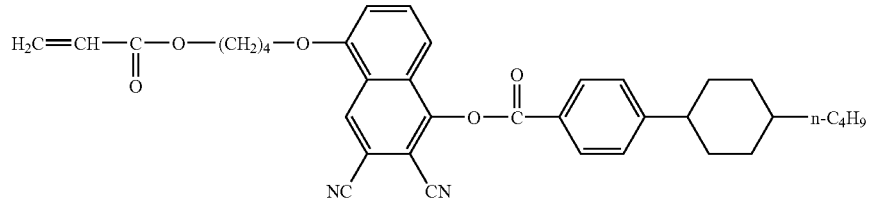
(1R)

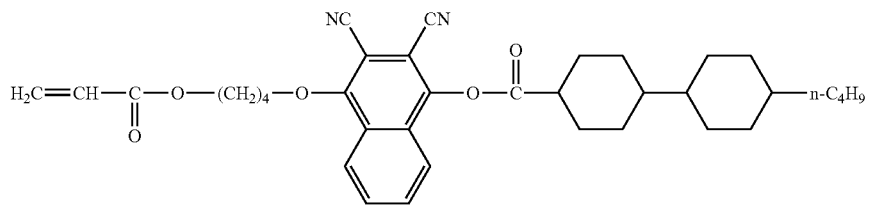

(1S)

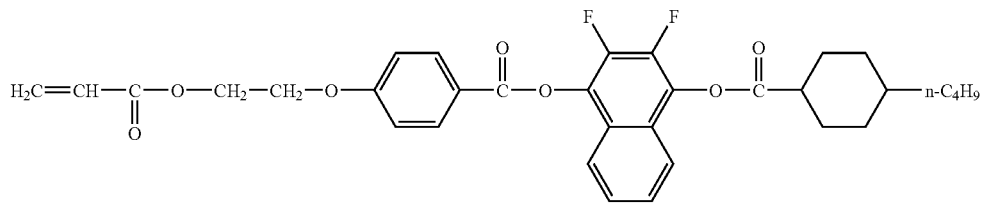

(1T)

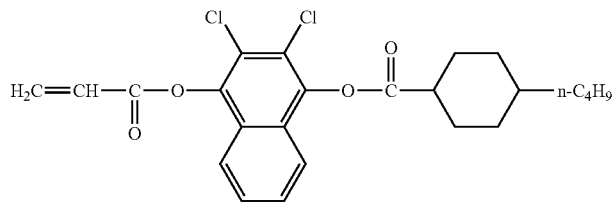

(1U)

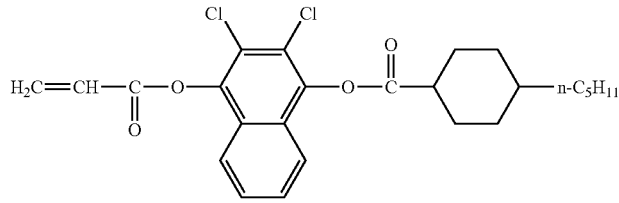

(1V)

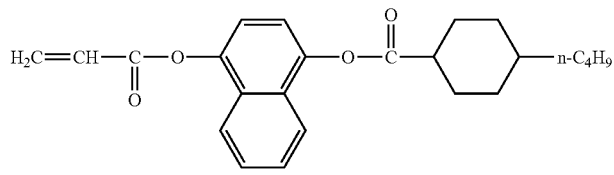

(1W)

In the above formula (2), $R^3$ is preferably a hydrogen atom from the same reason as for $R^1$.

$J^4$ is —$(CH_2)_t$O— or —$(CH_2)_u$O—CO—. Each of "t" and "u" which are independent of each other, is an integer of from 2 to 6.

$J^5$ is —O$(CH_2)_c$— or —COO—$(CH_2)_d$—. Each of "c" and "d" which are independent of each other, is an integer of from 2 to 6.

Each of $E^2$ and $E^3$ which are independent of each other, is a 1,4-phenylene group or a trans-1,4-cyclohexylene group. A hydrogen atom in such a group may be substituted by a chlorine atom, a fluorine atom, a methyl group or a cyano group. Each of $E^2$ and $E^3$ is preferably a non-substituted trans-1,4-cyclohexylene group, whereby the effect of the optical anisotropy of $W^2$ can be effectively utilized.

$W^2$ is a group similar to the above $W^1$, and its preferred embodiment is also the same.

The polymerizable compound (2) is preferably the following compound (2A) or (2B), whereby the effect of the optical anisotropy of $W^2$ can be effectively utilized.

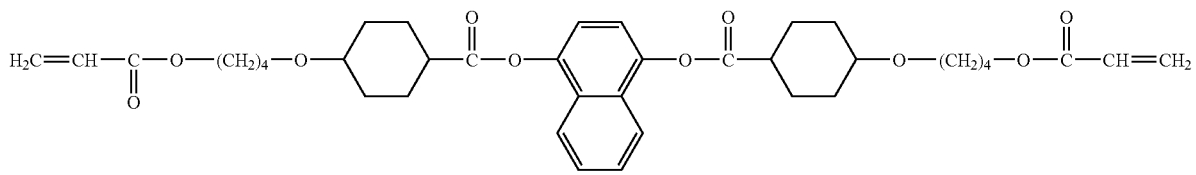

(2A)

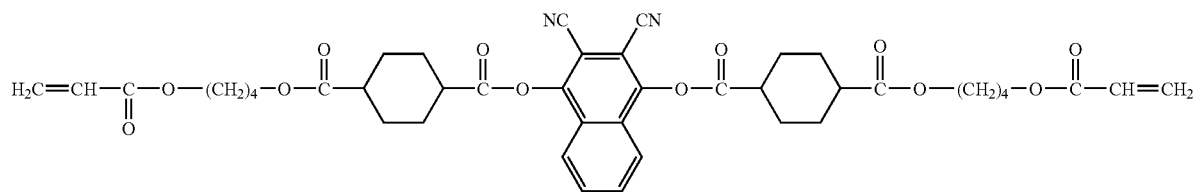

(2B)

In the present invention, preferred is a polymerizable liquid crystal composition containing at least two types of the polymerizable compound (1) and/or the polymerizable compound (2), whereby it will be easy to adjust the wavelength dispersion of the refractive index anisotropy depending upon the purpose of use in a broadband range.

Particularly, in the present invention, preferred is a polymerizable liquid crystal composition containing at least two types of the polymerizable compounds (1), and particularly preferred is a polymerizable liquid crystal composition containing three or four types of the polymerizable compounds (1). Specifically, preferred is a polymerizable liquid crystal composition containing the above compounds (1A) to (1C), a polymerizable liquid crystal composition containing the above compounds (1A) to (1C) and (1U), or a polymerizable liquid crystal composition containing the above compounds (1D) and (1W).

In the polymerizable liquid crystal composition of the present invention, the content of the polymerizable compound is preferably at least 10 mass % based on the polymerizable liquid crystal composition, more preferably from 20 to 100 mass %, particularly preferably from 50 to 100 mass %. It is considered that the higher the content of the polymerizable compound, the better the wavelength dispersion properties of the refractive index anisotropy.

Further, the polymerizable liquid crystal composition of the present invention may contain a compound other than the above polymerizable compound (hereinafter referred to as "another compound"). Such another compound may, for example, be a polymerizable liquid crystalline compound or a polymerizable non-liquid crystalline compound other than the above polymerizable compound.

The polymerizable liquid crystalline compound is not particularly limited so long as it is a compound having a mesogen structure and a polymerizable functional group and exhibiting liquid crystallinity. It may, for example, be an acrylate compound, a methacrylate compound, a siloxane compound or an epoxy compound, and it is preferably an acrylate compound or a methacrylate compound having favorable photopolymerization properties.

Further, in a case where another polymerizable liquid crystalline compound has a plurality of polymerizable functional groups, the polymerizable functional groups may be the same or different. Particularly, a compound having two polymerizable functional groups is preferred, whereby favorable heat resistance and strength properties will be obtained.

As another polymerizable liquid crystalline compound, specifically, the following compounds (30), (40) and (50), etc. (see e.g. JP-A-10-265531) may, for example, be mentioned.

Compound (30):

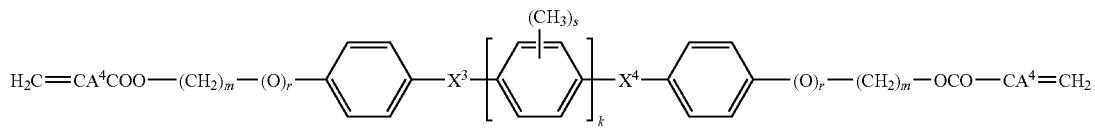

wherein $A^4$ is a fluorine atom, a chlorine atom, a hydrogen atom or a methyl group, m is an integer of from to 8, r is 0 when m is 0 or 1, and r is 1 when m is an integer of from 2 to 8, $X^3$ is a single bond, —COO—, —OCO— or —CH$_2$CH$_2$—, s is 0 or 1, k is 0 or 1, and $X^4$ is a single bond when k is 0, and $X^4$ has the same structure as $X^3$ when k is 1;

Compound (40):

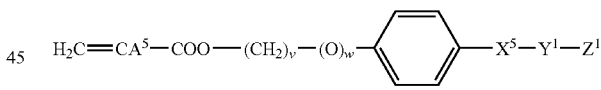

wherein $A^5$ is a fluorine atom, a chlorine atom, a hydrogen atom or a methyl group, v is an integer of from 0 to 8, w is 0 when v is 0 or 1, and w is 1 when v is an integer of from 2 to 8, $X^5$ is a single bond, —COO—, —OCO— or —CH$_2$CH$_2$—, $Y^1$ is a 1,4-phenylene group or a trans-1,4-cyclohexylene group, and $Z^1$ is a $C_{1-8}$ alkoxyl group, a fluorine atom, a chlorine atom or a cyano group.

Further, as another polymerizable liquid crystalline composition, a compound represented by the following formula may, for example, be also mentioned.

Compound (50):

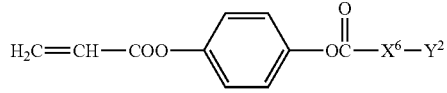

wherein $X^6$ is a 1,4-phenylene group or a trans-1,4-cyclohexylene group, and $Y^2$ is a $C_{1-8}$ alkyl group.

As the compound (30), the following compounds are preferred:

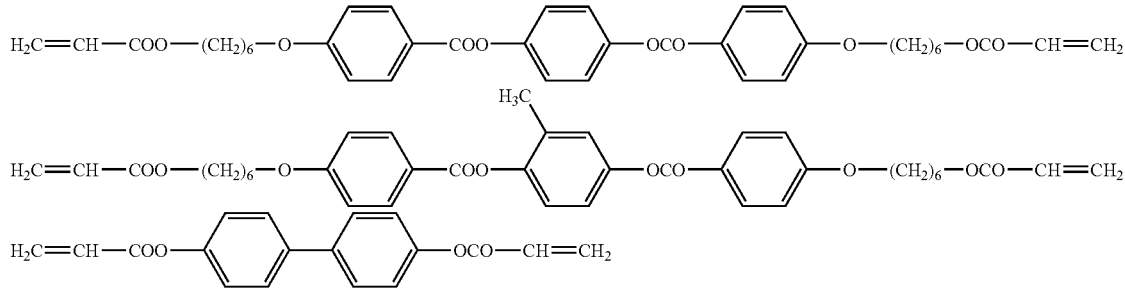

As the compound (40), the following compounds are preferred:

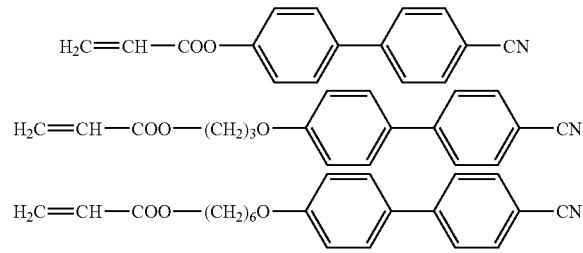

As the compound (50), the following compounds (a 1,4-phenylene group is represented by Ph, and a trans-1,4-cyclohexylene group is represented by Cy):

$H_2C=CH-COO$-Ph-OCO-Cy-n-$C_3H_7$
$H_2C=CH-COO$-Ph-OCO-Cy-n-$C_4H_9$
$H_2C=CH-COO$-Ph-OCO-Cy-n-$C_5H_{11}$
$H_2C=CH-COO$-Ph-OCO-Ph-n-$C_3H_7$
$H_2C=CH-COO$-Ph-OCO-Ph-n-$C_4H_9$
$H_2C=CH-COO$-Ph-OCO-Ph-n-$C_5H_{11}$

The polymerizable non-liquid crystalline compound may, for example, be an acrylate, a methacrylate or a vinyl ether. The amount of their use is preferably at most 5 mass %, particularly preferably at most 1 mass % based on the polymerizable liquid crystal composition.

The polymerizable liquid crystal composition of the present invention preferably contains a polymerization initiator in order that the after-mentioned polymerization reaction will smoothly proceed.

The polymerization initiator may, for example, be a thermal polymerization initiator such as a peroxide or an azo compound; or a photopolymerization initiator such as an acetophenone, a benzophenone, a benzoin, a benzyl, a Michler's ketone, a benzoin alkyl ether, a benzyl dimethyl ketal or a thioxanthone, and they may be used alone or in combination of two or more of them. The amount of the polymerization initiator is preferably from 0.1 to 10 mass %, particularly preferably from 0.3 to 2 mass % based on the polymerizable liquid crystal composition.

Further, the polymerizable liquid crystal composition of the present invention may contain a stabilizer, a ultraviolet absorber or the like. The stabilizer may, for example, be hydroquinone, a hydroquinone monoalkyl ether or a tert-butyl catechol, and they may be used alone or in combination of two or more of them. The content of the stabilizer, the ultraviolet absorber or the like is preferably at most 1 mass %, particularly preferably at most 0.5 mass % based on the polymerizable liquid crystal composition.

The optical anisotropic material of the present invention is an optical anisotropic material obtained by polymerizing the above polymerizable liquid crystal composition of the present invention. The polymerization reaction is carried out preferably in such a state that the above polymerizable liquid crystal composition is injected into a cell subjected to alignment treatment so that the liquid crystal in the composition is aligned. The polymerization reaction may, for example, be photopolymerization reaction or thermal polymerization reaction, preferably photopolymerization reaction.

Light to be used for the photopolymerization reaction may, for example, be ultraviolet rays or visible rays, preferably ultraviolet rays. Further, in the case of photopolymerization reaction, polymerization will efficiently proceed when the above photopolymerization initiator is used.

The optical anisotropic material of the present invention is preferably a material which is optically uniaxial and of which the value of the refractive index anisotropy Δn which is a difference between the ordinary refractive index $n_o$ and the extraordinary refractive index $n_e$ increases as the wavelength of light to be used increases. Generally, when the refractive index anisotropy is constant regardless of the wavelength, the phase difference caused by the refractive index anisotropy decreases as the wavelength of light increases.

Accordingly, when a phase plate or a diffraction element is optimized at a specific wavelength, the phase plate may not function as a phase plate or the efficiency of the diffraction element may decrease, along with an increase of the wavelength of light to be used. On the other hand, in the case of a material of which the refractive index anisotropy increases as the wavelength of light to be used increases, the decrease in the phase difference accompanying the increase of the wavelength of light can be suppressed, whereby it can sufficiently function as a phase plate or a diffraction element in a broadband range. Namely, it can be suitably used as an optical element which controls polarization state and/or phase state of light to be used in a certain wavelength region.

The optical element of the present invention is an optical element to control polarization state and/or phase state of light to be used, formed by using the optical anisotropic material of the present invention.

Such an optical element may, for example, be a phase plate or a polarizing diffraction element. The phase plate not only controls the phase of laser beam at a single wavelength but also can be preferably used as a broadband phase plate to control phase of laser beams at plural wavelengths in a certain wavelength region. As the polarizing diffraction element, a diffraction element which provides high diffraction efficiency at any wavelength among plural wavelengths used, or a diffraction element through which a laser beam at a specific wavelength is transmitted and which diffracts only laser beam at a specific wavelength, can be realized. Specific examples of the polarizing diffraction element include a polarizing beam splitter and a polarizing prism. They may be made to have light focusing or divergent function or to have wavelength selectivity.

As is evident from after-mentioned Example 5 and FIG. 1 (a graph illustrating the wavelength dependence of the refractive index anisotropy of a phase plate obtained in Example 5), the optical anisotropic material of the present invention is excellent in the above wavelength dispersion properties in that the refractive index anisotropy increases as the wavelength of light increases, and the phase plate of the present invention formed by using such an optical anisotropic material is capable of controlling wavelength dispersion of a phase difference and is thereby very useful.

The phase plate of the present invention may, for example, be a quarter wave plate or a half wave plate. The quarter wave plate rotates by 90 degree the direction of the linearly polarized light after reflected on an optical recording medium and further transmitted through the quarter wave plate again, relative to the direction of the linearly polarized light before entering the quarter wave plate. Thus, by combining it with a polarizing diffraction element, optical properties such as occurrence or non-occurrence of diffracted light depending on the polarization direction can be controlled.

When a quarter wave plate is prepared as the phase plate of the present invention, it will sufficiently exhibit function to rotate the polarization direction of light in a wide wavelength region by 90 degree.

Further, the phase plate of the present invention may be used alone but is preferably used as stacked with another optical element to be used for an optical head device, whereby the number of members can be reduced, the optical head device can be downsized, and optical head device assembling process can be simplified. The optical element to be used as stacked with the phase plate may, for example, be a diffraction grating for three beams, an aperture limiting element which limits the diameter of light at a specific wavelength among plurality of wavelengths, or an aberration correction element which corrects wave aberration generated.

Further, when the phase plate of the present invention is used for an optical head device having an optical element utilizing the difference of properties by polarized light such as a polarizing diffraction element, particularly high effects will be obtained, and it is suitable as a component for an optical head device to which further downsizing and weight reduction are required.

The structure when the optical anisotropic material of the present invention is used as a polarizing diffraction element is generally as follows.

First, a polarizing diffraction element has a diffraction grating region which diffracts incident light in a specifically polarized state. This diffraction grating region comprises a first member made of a first material and a second member made of a second material, and the first member and the second member differ from each other in the refractive index to the above incident light in a specifically polarized state. Further, the first member and the second member are disposed alternately to be in contact with each other at a certain pitch. In the present invention, as this first material, the optical anisotropic material of the present invention is used.

Here, the first material and the second material are not necessarily different materials. However, the first member and the second member have to differ from each other in the refractive index to the above incident light in a specifically polarized state by e.g. different alignment direction of the materials in the respective members. As a process for preparing such a polarizing diffraction element, for example, the following processes may be mentioned.

(Process 1)

A process wherein the polymerizable liquid crystal composition of the present invention is sandwiched between a pair of substrates having an electrode such as a patterned ITO, subjected to alignment treatment in a predetermined direction, and a voltage is applied between electrodes to form two types of regions differing in the alignment direction in the polymerizable liquid crystal composition so that the two types of regions are alternately aligned at a certain pitch, followed by polymerization. In this case, both first member and second member are made of the optical anisotropic material of the present invention, but the respective members differ in the refractive index to incident light by the difference in the alignment state, and a diffraction grating region can be formed resultingly.

(Process 2)

A process in which the polymerizable liquid crystal composition of the present invention is applied to the surface of the substrate subjected to alignment treatment in a predetermined direction, followed by polymerization to prepare an optical anisotropic material, and further, a concavo-convex grating structure is formed on the surface of the optical anisotropic material, and concave portions in the grating are filled with an optical isotropic material (JP-A-11-211905). In this process, either polymerization of the polymerizable liquid crystal composition of the present invention or forming of concavo-convex grating shape may be carried out first. Further, it is possible to carry out polymerization reaction in a state where the polymerizable liquid crystal composition is sandwiched between two facing substrates, peel off one substrate and then to form a concavo-convex grating structure.

(Process 3)

A process wherein a concavo-convex grating structure is formed on the surface of an optical isotropic material, and concave portions of the grating are filled with the polymerizable liquid crystal composition of the present invention, followed by polymerization.

The concavo-convex grating structure can be formed by e.g. an etching method by photolithography, a dry etching method, or a pressing method by a mold having a grating shape.

The grating height of the diffraction grating in the polarizing diffraction element of the present invention is preferably from 1 to 40 μm, more preferably from 2 to 20 μm. When the grating height is within this range, the polarizing diffraction element can easily be produced. Further, the polarizing diffraction element of the present invention can be a polarizing diffraction element having a desired diffraction efficiency by optionally changing the grating height.

Further, the concave portions of the grating in the grating structure can be filled with the polymerizable liquid crystal composition or an optical isotropic material (such as a photopolymerizable acrylic resin or epoxy resin) by a method such as spin coating. Even when the substrate itself has convexes and concaves, it is preferred to use a substrate subjected to rubbing treatment as the substrate, whereby alignment disturbance at the time of filling and polymerization will not occur.

Further, the polarizing diffraction element of the present invention is preferably a polarizing diffraction element comprising an optical anisotropic material having a concavo-convex grating structure on its surface, at least concave portions of the concave and convex portions in the grating structure filled with an optical isotropic material having a refractive index $n_s$ equal to the ordinary refractive index $n_o$ of the above optical anisotropic material. Such a polarizing diffraction element can be prepared by the above Process 2 or 3.

A polarizing diffraction element obtained by filling with an optical isotropic material having a refractive index $n_s$ equal to the ordinary refractive index $n_o$ of the optical anisotropic material of the present invention, functions as a diffraction grating in some cases and does not function in other cases, depending upon the polarization direction of transmitting light.

That is, when concave portions are filled with an optical isotropic material having a refractive index $n_s$ equal to the ordinary refractive index $n_o$ of the optical anisotropic material of the present invention, when linearly polarized light in a direction which produces ordinary refractive index is made to enter the polarizing diffraction element, there will be no difference in the refractive index between the optical anisotropic material and the optical isotropic material, and there will be no diffraction effect. Whereas, when light linearly polarized in a direction which produces an extraordinary refractive index, at an angle of 90° with the above direction, is made to enter the diffraction element, there will be a difference between the refractive index between the optical anisotropic material and the optical isotropic material, and there will be diffraction effect.

The polarizing diffraction element of the present invention is excellent in that the diffraction efficiency does not substantially depend on the wavelength, since the decrease in the phase difference accompanying the increase of the wavelength of light is suppressed.

Further, when the optical anisotropic material of the present invention is used to prepare a polarizing diffraction element used in a certain wavelength range, such a material is preferably a material which provides a zero value of the refractive index anisotropy to light at a specific wavelength among a plurality of wavelengths used and provides a great value of the refractive index anisotropy to light at other wavelengths, whereby a wavelength-selective diffraction hologram having wavelength selectivity in addition to polarization selectivity can be prepared by combining an optical isotropic material having an appropriate refractive index.

In recent years, a plurality-wavelength-compatible optical head device is commercialized, which can read or write information recorded on optical disks such as DVD and CD which are optical recording media differing in the standard, in various optical head devices on which a semiconductor laser for DVD, a semiconductor laser for CD and further a blue semiconductor laser are mounted.

In the optical head device, to modulate the phase state of a laser beam, a broadband phase plate which imparts a certain constant phase difference to laser beams at a plurality of wavelengths is required. Further, in such an optical head device, it is required that one light-receiving element can be used for light at a plurality of wavelengths, to reduce the number of components and to simplify the signal treatment. For example, in order to detect signal light corresponding to light at two to three different wavelengths of optical recording disks (HD DVD, BD) using blue laser beam, DVD and CD by a common light-receiving element, two or three polarizing diffraction elements differing in the grating period properly designed according to the respective wavelengths are required.

According to the phase plate and the polarizing diffraction element of the present invention, a single phase plate can be applied to an optical head device using light at a plurality of wavelengths, and light at a plurality of wavelengths can effectively be diffracted by a single diffraction element. The optical head device may, for example, have the following embodiment.

The optical head device comprises two or more semiconductor lasers each emitting linearly polarized laser beams at two or more wavelengths, an objective lens focusing the above laser beams emitted from the semiconductor lasers on an optical recoding medium, and a phase plate controlling the phase state of the laser beams, disposed between the semiconductor laser and the objective lens. As the above phase plate, the phase plate of the present invention is used.

Further, the optical head device comprises two or more semiconductor lasers, each emitting linearly polarized laser beams at two or more wavelengths, an objective lens focusing the above laser beams on an optical recording medium, a polarizing diffraction element diffracting light reflected on the optical recording medium, and a photodetector detecting the diffracted emitted light. As the polarizing diffraction element, the polarizing diffraction element of the present invention is used.

Figure 3:
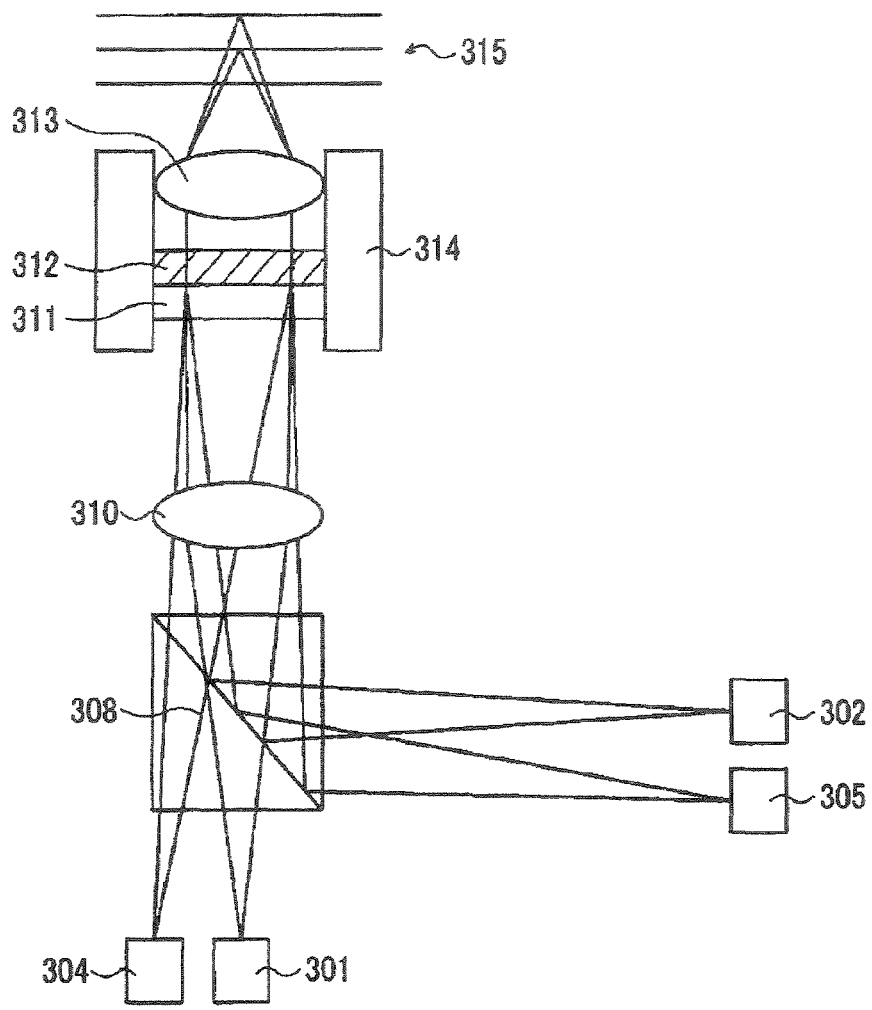
FIG. 3 is a side view schematically illustrating one example of an optical head device to which the phase plate and the polarizing diffraction element of the present invention are applied.

A side view schematically illustrating one example of an optical head device to which the phase plate and the polarizing diffraction element of the present invention are applied is shown in FIG. 3. In this optical head device, linearly polarized lights at wavelengths $\lambda^1$ and $\lambda^2$ emitted from semiconductor lasers 301 and 302, respectively, are combined by a light-combiner prism 308 which reflects light at wavelength $\lambda^2$ and which transmits light at wavelength $\lambda^1$, and the combined light is focused on and applied to an information recording surface of an optical disk 315 which is an optical recording medium, via a collimater lens 310, a polarizing diffraction element 311, a broadband phase plate 312 and an objective lens 313 held by an actuator 314. The returning beams of light reflected on the optical disk 315 containing information of pits formed on the information recording surface proceed back the respective paths.

Here, the broadband phase plate 312 is made of the optical anisotropic material of the present invention and functions as a quarter wave plate to both lights at wavelengths $\lambda^1$ and $\lambda^2$. Further, the polarizing diffraction element 311 also utilizes the optical anisotropic material of the present invention and thereby has a sufficient diffraction efficiency to both lights at wavelengths $\lambda^1$ and $\lambda^2$.

Namely, the polarization direction of the linearly polarized light of beams of light emitted from the semiconductor laser 302 as a light source for light at wavelength $\lambda^2$ is matched to a direction not to cause diffraction by the polarizing diffraction element 311, whereby the beams of light at wavelength $\lambda^2$ is linearly transmitted without being diffracted by the polarizing diffraction element 311 and enters the broadband phase plate 312, is converted to circularly polarized light with a phase difference of $\frac{1}{4}\lambda$ and applied to an optical disk. On the returning way, the returning beams of light in the form of reversely circularly polarized light reflected on the information recording surface is converted to linearly polarized light at right angles to the linearly polarized light before entering the polarizing diffraction element 311, by the broadband phase plate 312, and then diffracted by the polarizing diffraction element 311 and is introduced by a photodetector 305 via the collimater lens 310 and the light-combiner prism 308, and then information recorded on the optical disk 315 is read.

Further, regarding the wavelength $\lambda^1$, the linearly polarized laser beam emitted from the semiconductor laser 301 is transmitted through the light-combiner prism 308, and is focused on and applied to the optical disk 315 via the collimater lens 310, and the polarizing diffraction element 311, the broadband phase plate 312 and the objective lens 313 held by the actuator 314. The beams of light at wavelength $\lambda^1$, similar to the beams of light at wavelength $\lambda^2$, are converted to circularly polarized light with a phase difference of ¼$\lambda$ by the broadband phase plate 312 and applied to the optical disk 315. Therefore, the beams are converted to linearly polarized light at right angles to the linearly polarized light before entering the polarizing diffraction element 311, by the broadband phase plate 312 on the returning way. Further, similar to the returning beams of light at wavelength $\lambda^2$, the linearly polarized light is diffracted by the polarizing diffraction element 311, is transmitted through the collimater lens 310 and the light-combiner prism 308 and is introduced by the photodetector 304, whereby information recorded on the optical disk 315 is read.

The compound of the present invention has a short conjugation length in a direction at right angles to the condensed ring i.e. the molecular major axis direction, whereby its light resistance to short wavelength light improves. Therefore, it can be suitably used also for an optical element for an optical pickup for blue laser.

The above is description regarding an optical device for an optical pickup, but the present invention is not limited thereto, and is applicable to the other optical fields, including an optical element for communication, etc.

EXAMPLES

Now, the present invention will be described in further detail with reference to Examples.

Example 1

Preparation of Compound (1A)

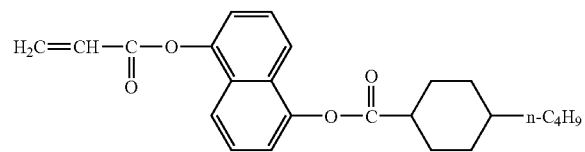

(1A)

Example 1-1

Example for Preparation of Compound (7)

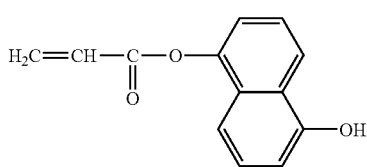

(7)

An acrylic chloride (19 g, 0.21 mol) was added to a mixture of 1,5-dihydroxynaphthalene (32 g, 0.2 mol), tetrahydrofuran (THF) (160 mL) and triethylamine (21.3 g, 0.21 mol) while cooling with ice water over a period of one hour. On that occasion, the reaction solution was vigorously stirred to keep the reaction temperature be at most 20° C. After stirring for 12 hours, the reaction solution was left at rest and subjected to filtration under reduced pressure, and the filtrate was vacuum concentrated.

Then, dichloromethane (100 mL) was added to the concentrated filtrate and left at rest. The precipitated solids were removed by filtration, and the filtrate was vacuum concentrated. Dichloromethane (50 mL) was added to the residue after concentration, and subjected to column chromatography (bulking agent: basic alumina, developing solvent: dichloromethane). After effusion of 1,5-diacryloyloxynaphthalene as a by-product was confirmed, basic alumina in the column was taken out, and 5% hydrochloric acid (400 mL) and dichloromethane (200 mL) were added, followed by stirring. After filtration under reduced pressure, the organic layer was separated, washed with water and dried over anhydrous magnesium sulfate. Then, the filtrate was vacuum concentrated to obtain compound (7) (2.38 g) (yield: 5.5%).

Example 1-2

Example for Preparation of Compound (1A)

Trans-4-n-butylcyclohexanecarboxylic acid (5.0 g, 0.027 mol) was dissolved in THF (150 mL), and triethylamine (5.5 g, 0.055 mol) and methanesulfonic acid chloride (3.15 g, 0.027 mol) were added thereto, followed by stirring at −25° C. for one hour. To this mixed solution, compound (7) (5.35 g, 0.025 mol) obtained in Example 1-1 and 4-dimethylaminopyridine (0.61 g, 0.005 mol) were added, followed by stirring at −10° C. for one hour.

Then, the reaction solution washed with a 10% sodium hydrogen carbonate aqueous solution and water, dried over anhydrous sodium sulfate and vacuum concentrated. The residue after concentration was subjected to silica gel column chromatography (developing solvent: dichloromethane) to obtain a fraction containing compound (1A). This fraction was concentrated and then recrystallized from a solvent mixture of hexane and toluene to obtain powdery crystals (2.96 g) of compound (1A). The yield was 31.2%.

The $^1$H-NMR spectrum (solvent: CDCl$_3$, internal standard: TMS) of compound (1A) was such that $\delta$ (ppm): 0.91 (3H, t), 1.07 (1H, m), 1.31 (8H, m), 1.67 (2H, m), 1.92 (2H, m), 2.26 (2H, m), 2.66 (1H, m), 6.13 (1H, d), 6.48 (1H, m), 6.71 (1H, d), 7.25 (2H, m), 7.48 (2H, d), 7.76 (2H, t).

Figure 4:
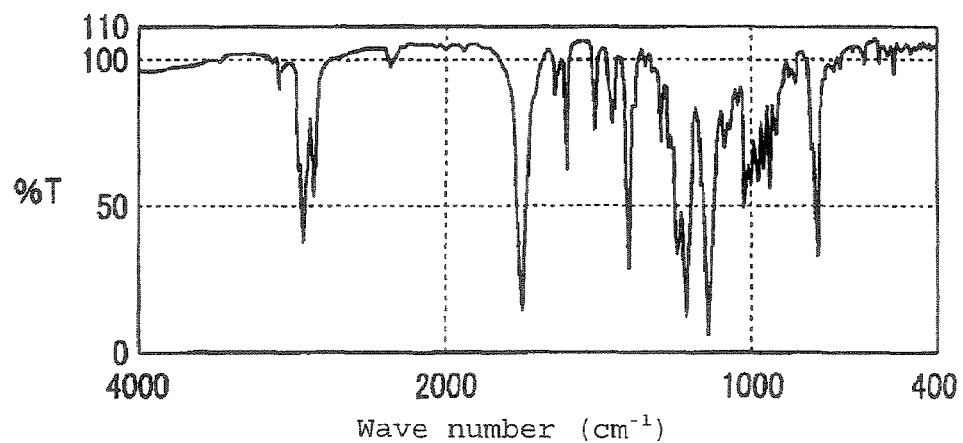
FIG. 4 is an infrared absorption spectrum of compound (1A).

As a result of observation of compound (1A) by a polarizing microscope, its phase changed from crystals to an isotropic liquid at 78° C. when the temperature was increased, and accordingly compound (1A) was confirmed not to exhibit liquid crystallinity. The infrared absorption spectrum (KBr disk) of compound (1A) is shown in FIG. 4.

Example 2

Preparation of Compound (1B)

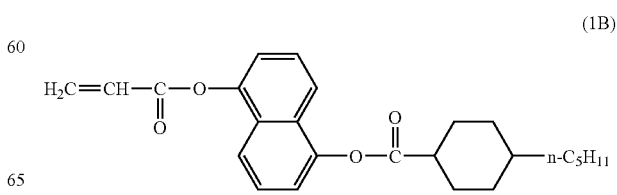

(1B)

Compound (1B) (5.3 g) was obtained in the same manner as in Example 1 except that trans-4-n-butylcyclohexanecarboxylic acid was changed to trans-4-n-pentylcyclohexanecarboxylic acid (5.5 g, 0.027 mol). The yield was 53.7%.

The $^1$H-NMR spectrum (solvent: CDCl$_3$, internal standard: TMS) of compound (1B) was such that δ (ppm): 0.90 (3H, t), 1.02 (1H, m), 1.30 (10H, m), 1.67 (2H, m), 1.91 (2H, m), 2.27 (2H, m), 2.65 (1H, m), 6.08 (1H, t), 6.45 (1H, m), 6.69 (1H, d), 7.25 (2H, m), 7.49 (2H, m), 7.76 (2H, m).

Figure 5:
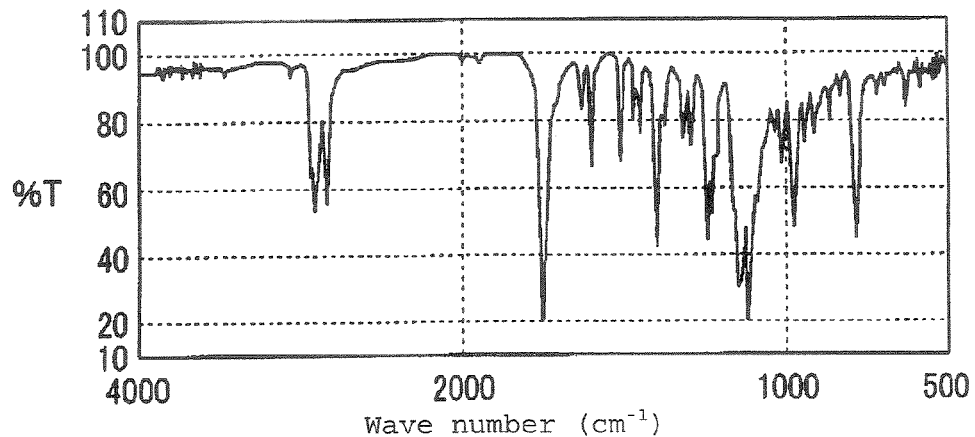
FIG. 5 is an infrared absorption spectrum of compound (1B).

As a result of observation of compound (1B) by a polarizing microscope, its phase changed from crystals to an isotropic liquid at 85.1° C. when the temperature was increased, and changed from an isotropic liquid to a nematic phase at 60.7° C. when the temperature was decreased, and accordingly compound (1B) was confirmed to have liquid crystallinity. The infrared absorption spectrum (KBr disk) of compound (1B) is shown in FIG. 5.

Example 3

Preparation of Compound (1C)

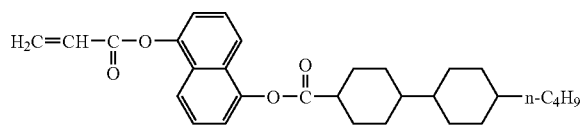

(1C)

Compound (1C) (5.16 g) was obtained in the same manner as in Example 1 except that trans-4-n-butylcyclohexanecarboxylic acid was changed to trans-4-(trans-4-n-butylcyclohexyl)cyclohexanecarboxylic acid (7.3 g, 0.027 mol). The yield was 44.6%.

The $^1$H-NMR spectrum (solvent: CDCl$_3$, internal standard: TMS) of compound (1C) was such that δ (ppm): 0.91 (3H, t), 0.87 to 1.28 (14H, m), 1.62 to 1.92 (10H, m), 2.28 (1H, m), 2.65 (1H, m), 6.13 (1H, d), 6.49 (1H, m), 6.71 (1H, d), 7.26 (2H, m), 7.48 (2H, m), 7.77 (2H, t).

Figure 6:
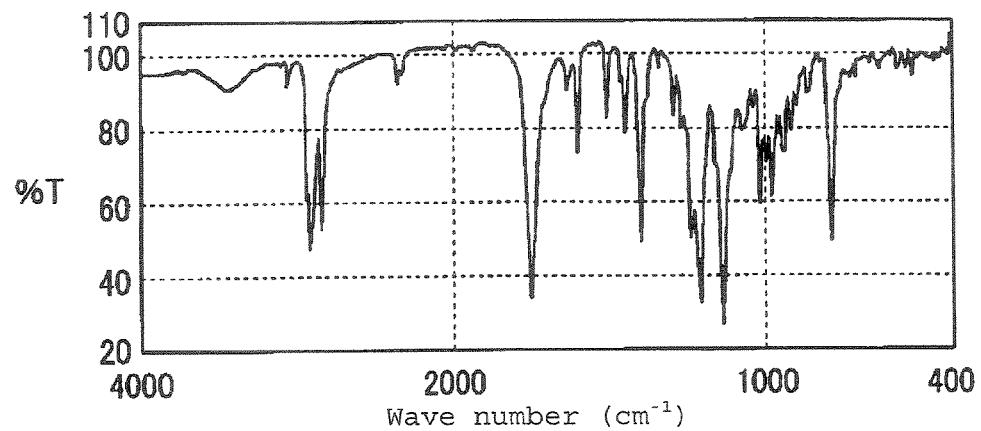
FIG. 6 is an infrared absorption spectrum of compound (1C).

As a result of observation of compound (1C) by a polarizing microscope, its phase changed from crystals to a nematic phase at 104° C. and from a nematic phase to an isotropic liquid at 193° C. when the temperature was increased, and accordingly the compound (1C) was confirmed to have liquid crystallinity. The infrared absorption spectrum (KBr disk) of compound (1C) is shown in FIG. 6.

Example 4

Preparation of Compound (2B)

Trans-1,4-cyclohexanedicarboxylic acid (17.2 g), thionyl chloride (47.5 g) and toluene (200 mL) were charged in a reactor, followed by stirring under reflux, and surplus tionyl chloride was removed by azeotropic distillation together with toluene to obtain trans-1,4-cyclohexane-dicarboxylic acid chloride.

Then, the above-obtained trans-1,4-cyclohexane-dicarboxylic acid chloride and dichloromethane (100 mL) were charged in a reactor, followed by stirring, and a solution comprising 4-hydroxybutyl acrylate (14.4 g), pyridine (7.9 g) and dichloromethane (150 mL) was dropwise added under cooling with ice water, followed by stirring further for one hour.

Then, this reaction solution was added to diluted hydrochloric acid, followed by extraction with dichloromethane and washing with water, and then the solvent was distilled off. The residue after distillation was treated with a sodium hydrogen carbonate aqueous solution and washed with THF. The aqueous layer was separated and acidified with a 5% hydrochloric acid, and the resulting precipitates were extracted with dichloromethane. The dichloromethane layer washed with water and dried over magnesium sulfate, and the solvent was distilled off to obtain residue 1.

Then, the above residue 1 (6.5 g), thionyl chloride (9.5 g) and dichloromethane (100 mL) were charged to a reactor, followed by stirring under reflux, and surplus thionyl chloride was removed by azeotropic distillation together with dichloromethane to obtain residue 2.

Then, the above obtained residue 2 and dichloromethane (100 mL) were charged in a reactor, followed by stirring, and a solution comprising 1,4-dihydroxynaphthalene-2,3-dicarbonitrile (2.1 g), pyridine (1.5 g) and tetrahydrofuran (150 mL) was dropwise added under cooling with ice water, followed by stirring further for one hour.

Then, the reaction solution was added to diluted hydrochloric acid, extracted with dichloromethane, washed with water and dried over magnesium sulfate, and then the solvent was distilled off. The residue after distillation was purified by column chromatography (bulking agent: silica gel, developing solvent: THF). A fraction containing the aimed product was concentrated and recrystallized from a solvent mixture of dichloromethane and toluene to obtain powdery crystals of compound (2B).

The $^1$H-NMR spectrum (solvent: CDCl$_3$, internal standard: TMS) of compound (2B) was such that δ (ppm): 1.75 (16H, m), 2.37 (10H, m), 2.84 (2H, m), 4.19 (8H, m), 5.83 (2H, m), 6.12 (2H, m), 6.44 (2H, m), 7.84 (2H, m), 7.94 (2H, m).

Figure 7:
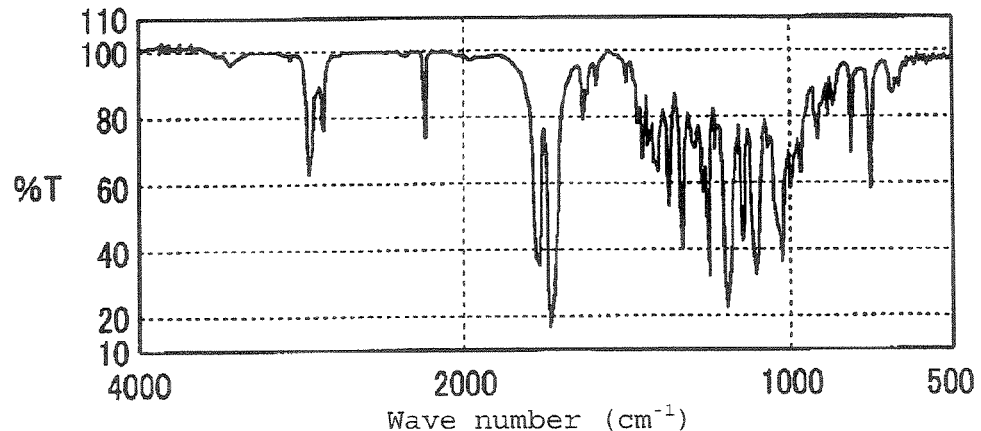
FIG. 7 is an infrared absorption spectrum of compound (2B).

As a result of observation of compound (2B) by a polarizing microscope, its phase changed from crystals to an isotropic liquid at 176° C. when the temperature was increased, and accordingly compound (2B) was confirmed not to have liquid crystallinity. The infrared absorption spectrum (KBr disk) of compound (2B) is shown in FIG. 7.

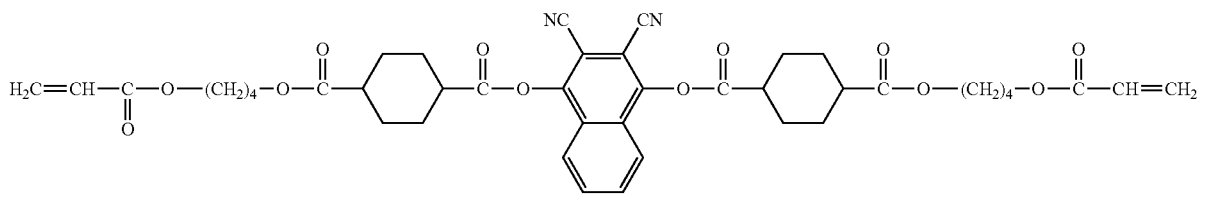

(2B)

Example 5

Preparation of Compound (1U)

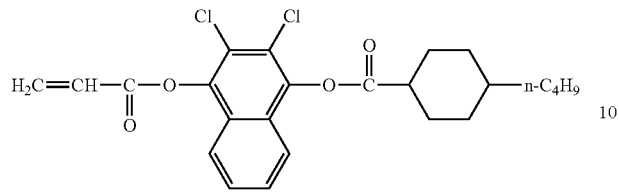

Example 5-1

Example for Preparation of Compound (11)

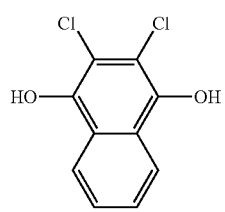

An aqueous (800 ml) solution of $Na_2S_2O_4$ (87 g) was charged in a three-necked flask equipped with a thermometer and a stirrer, and a THF (800 mL) solution of 2,3-dichloro-1,4-naphthoquinone (22.7 g, 0.1 mol) was added over a period of 10 minutes, followed by stirring at 20° C. for an hour. After the reaction, dichloromethane was added, followed by washing with water twice. The organic layer was dried over anhydrous magnesium sulfate, and the solvent was removed by a rotary evaporator. The residue was recrystallized from toluene (250 mL) to obtain compound (11) (20.2 g). The yield was 88%. The melting point of compound (11) was 153.1° C.

Example 5-2

Example for Preparation of Compound (12)

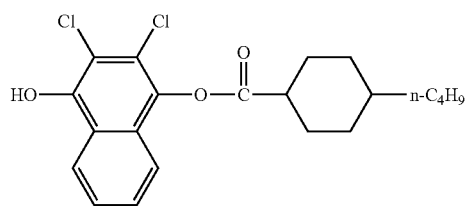

Then, a dichloromethane solution of trans-4-n-butylcyclohexanecarboxylic acid chloride obtained by reacting trans-4-n-butylcyclohexanecarboxylic acid (12 g, 0.065 mol) and thionyl chloride (15.5 g) in dichloromethane (150 mL) was dropped to a THF (160 ml) solution of pyridine (5.5 mL) and compound (11) (15 g, 0.065 mol) obtained in Example 5-1. The dropping was carried out over a period of 30 minutes under cooling with an ice bath maintained at 5° C. The precipitated pyridine hydrochloride was removed, dichloromethane (300 mL) was added to the solution, and the solution was washed with a 5% $NaHCO_3$ aqueous solution and then washed with water twice. The solution was dried over anhydrous magnesium sulfate and concentrated. The residue after the concentration was dissolved in dichloromethane (100 mL) and subjected to column chromatography (bulking agent: neutral silica gel, developing solvent: dichloromethane) to obtain compound (12) (2.3 g). The yield was 9%.

Example 5-3

Example for Preparation of Compound (1U)

Acrylic chloride (0.595 mL, 0.0073 mol) was added to a mixture of compound (12) (2.0 g, 0.005 mol) obtained in Example 5-2, THF (100 mL) and pyridine (0.625 mL, 0.0073 mol) while cooling with ice water over a period of 30 minutes. On that occasion, the reaction liquid was vigorously stirred to keep the temperature be at most 20° C. After stirring for 12 hours, the reaction liquid was subjected to filtration under reduced pressure, and the filtrate was vacuum concentrated. The residue after the concentration was purified by silica gel column chromatography (developing solvent: dichloromethane) and recrystallized from a solvent mixture of hexane and toluene to obtain compound (1U) (0.2 g). The yield was 8.9%.

The $^1$H-NMR spectrum (solvent: $CDCl_3$, internal standard: TMS) of compound (1U) was such that δ (ppm): 0.91 (3H, t), 1.07 (2H, m), 1.31 (7H, m), 1.75 (2H, m), 1.94 (2H, m), 2.31 (2H, m), 2.74 (1H, m), 6.18 (1H, d), 6.50 (1H, m), 6.82 (1H, d), 7.55 (2H, m), 7.77 (2H, m).

Figure 8:
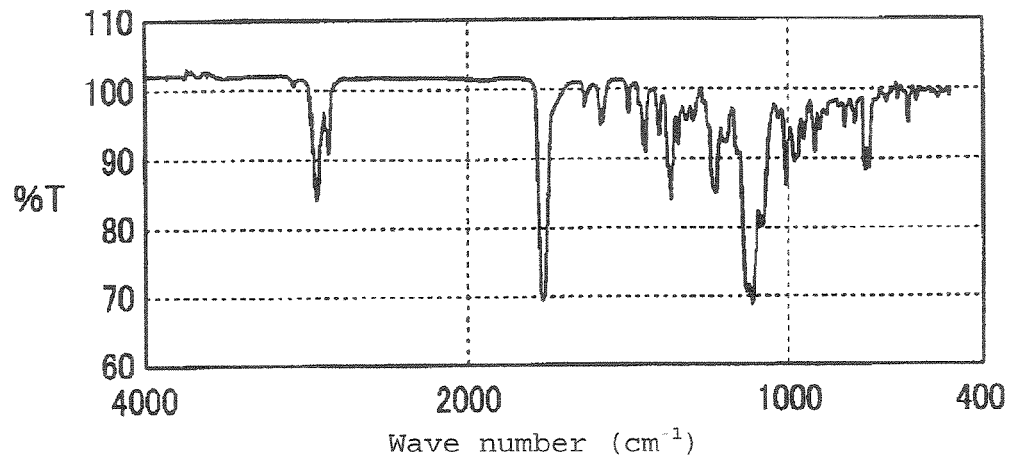
FIG. 8 is an infrared absorption spectrum of compound (1U).

As a result of observation of compound (1U) by a polarizing microscope, its phase changed from crystals to an isotropic liquid at 110° C. when the temperature was increased. The infrared absorption spectrum of compound (1U) is shown in FIG. 8.

Example 6

Preparation of Compound (1V)

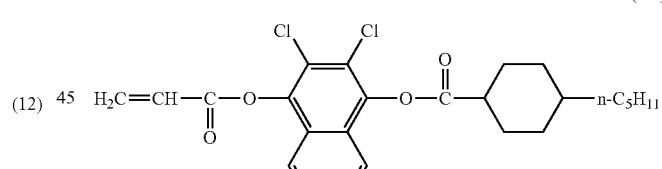

Example 6-1

Example for Preparation of Compound (13)

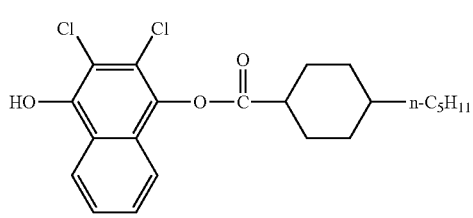

Compound (13) (3 g) was obtained in the same manner as in Example 5-2 except that trans-4-n-butylcyclohexanecarboxylic acid was changed to trans-4-n-pentylcyclohexanecarboxylic acid (8.7 g, 0.044 mol). The yield was 16.6%.

Example 6-2

Example for Preparation of Compound (1V)

Compound (1V) (0.5 g) was obtained in the same manner as in Example 5-3 except that compound (12) was changed to compound (13) (3 g, 0.0065 mol). The yield was 17.1%.

The $^1$H-NMR spectrum (solvent: CDCl$_3$, internal standard: TMS) of compound (1V) was such that δ (ppm): 0.91 (3H, t), 1.27 (11H, m), 1.75 (2H, m), 1.94 (2H, m), 2.31 (2H, m), 2.74 (1H, m), 6.18 (1H, d), 6.50 (1H, m), 6.82 (1H, d), 7.55 (2H, m), 7.77 (2H, m).

Figure 9:
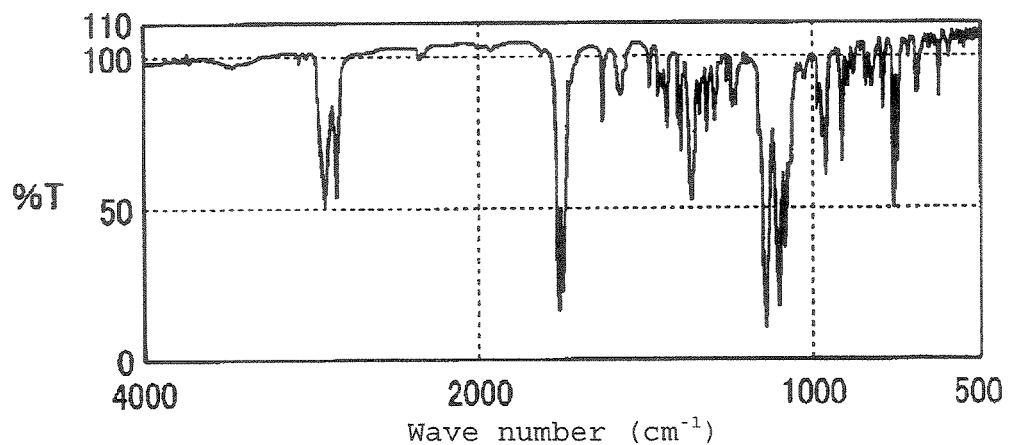
FIG. 9 is an infrared absorption spectrum of compound (1V).

As a result of observation of compound (1V) by a polarizing microscope, its phase changed from crystals to an isotropic liquid at 127° C. when the temperature was increased. The infrared absorption spectrum of compound (1V) is shown in FIG. 9.

Example 7

Example (1) for Preparation of Phase Plate

Compounds (1A), (1B) and (1C) obtained in Examples 1 to 3 were mixed in a ratio of 3:4:3 (molar ratio) to obtain liquid crystal composition A. Then, a photopolymerization initiator (tradename: Irgacure907, manufactured by Ciba Specialty Chemicals) was added to liquid crystal composition A in an amount of 0.5 mass % based on liquid crystal composition A to obtain liquid crystal composition A1.

Liquid crystal composition A1 was injected to an evaluation cell manufactured by EHC at 90° C., and irradiated with ultraviolet rays at a wavelength of 365 nm at 25° C. for 60 seconds to photopolymerize the composition to prepare a phase plate A.

Glass on a plane of the phase plate A was released by a razor, and refractive indices to laser beams at wavelengths of 412 nm, 633 nm and 780 nm were measured by a measuring machine (tradename: PRISMCOUPLER, manufactured by METRICON).

The refractive index anisotropy of the phase plate A was calculated from the difference between the refractive index in a direction in parallel with the alignment direction and the refractive index in a direction at right angles to the alignment direction. The result is shown in FIG. 1. It is confirmed that the value of the refractive index anisotropy of the phase plate A increases as the wavelength of the laser beam increases.

Example 8

Example (2) for Preparation of Phase Plate

Compounds (1A), (1B), (1C) and (1U) obtained in Examples 1 to 3 and 5 were mixed in a ratio of 6:8:6:5 (molar ratio) to obtain liquid crystal composition B. Then, a photopolymerization initiator (tradename: Irgacure907, manufactured by Ciba Specialty Chemicals) was added to liquid crystal composition B in an amount of 0.5 mass % based on liquid crystal composition B to obtain liquid crystal composition B1. Using liquid crystal composition B1, a phase plate B was prepared in the same manner as in Example 7.

Figure 2:
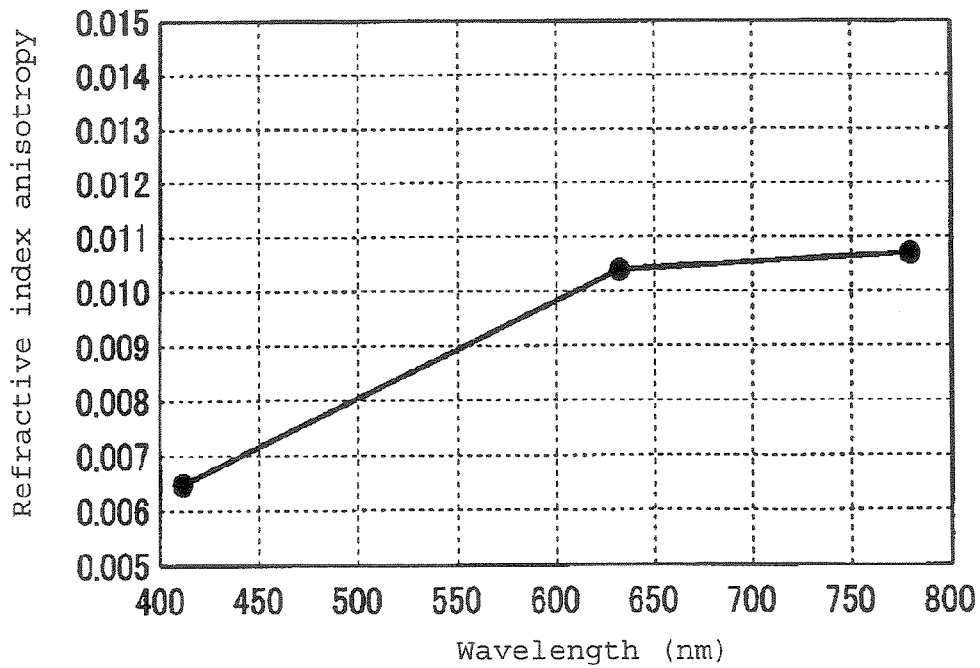
FIG. 2 is a graph illustrating the wavelength dependence of the refractive index anisotropy of a phase plate B obtained in Example 8.

In the same manner as in Example 7, regarding the phase plate B, refractive indices to laser beams at wavelengths of 412 nm, 633 nm and 780 nm were measured to calculate the value of the refractive index anisotropy. The result is shown in FIG. 2. It was confirmed that the value of the refractive index anisotropy of the phase plate B increases as the wavelength of the laser beam increases.

Example 9

Preparation of Compound (1D)

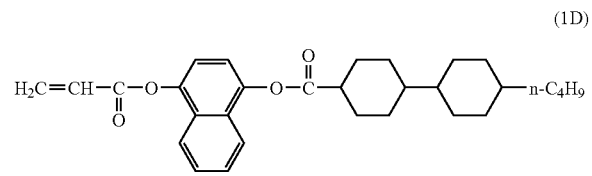

(1D)

Example 9-1

Preparation of Compound (14)

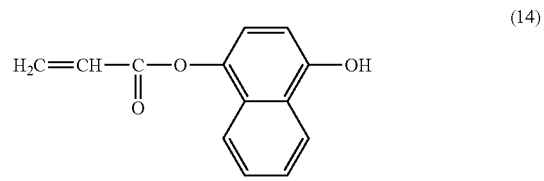

(14)

Acrylic chloride (19 g, 0.21 mol) was added to a mixture of 1,4-dihydroxynaphthalene (32 g, 0.2 mol), THF (160 mL) and triethylamine (21.3 g, 0.21 mol) under cooling with ice water over a period of one hour. On that occasion, the reaction solution was vigorously stirred to keep the reaction temperature be at most 20° C. After stirring for 12 hours, the reaction solution was left to stand and subjected to filtration under reduced pressure.

The filtrate was vacuum concentrated, and ethyl acetate (400 mL) was added to the residue, followed by washing with a 5% NaHCO$_3$ aqueous solution and washing with water twice. The organic layer was separated, dried over anhydrous magnesium sulfate and concentrated. Dichloromethane (400 mL) was added to the residue after the concentration, cooled and left at rest. The precipitated solids were removed by filtration, and the filtrate was vacuum concentrated and purified by column chromatography (bulking agent: neutral silica gel, developing solvent: dichloromethane) to obtain compound (14) (5.28 g). The yield was 12.4%.

Example 9-2

Example for Preparation of Compound (1D)

To trans-4-(trans-4-n-butylcyclohexyl)cyclohexanecarboxylic acid (2.9 g, 0.011 mol), dichloromethane (40 mL), thionyl chloride (11.9 g, 0.1 mol) and dimethylformamide (several drops) were added, followed by stirring at room temperature for 2 hours and distillation under reduced pressure to obtain pale yellow solids.

A mixture of the above pale yellow solids and THF (30 mL) was added to a mixture of compound (14) (2.1 g, 0.01 mol)

obtained in Example 9-1, THF (30 mL) and triethylamine (1.1 g, 0.011 mol) under cooling with ice water over a period of 30 minutes. On that occasion, the reaction solution was vigorously stirred to keep the reaction temperature be at most 5° C. After stirring for 3 hours, the reaction solution was left at rest and subjected to filtration under reduced pressure.

The filtrate was vacuum concentrated, and ethyl acetate (200 mL) was added to the residue to dissolve it, and the solution washed with a 5% NaHCO$_3$ aqueous solution and then washed with water twice. The organic layer was separated, dried over anhydrous magnesium sulfate and concentrated. The residue after the concentration was subjected to column chromatography (bulking agent: neutral silica gel. developing solvent: dichloromethane) to obtain a fraction containing compound (1D). This fraction was concentrated and recrystallized from ethyl acetate to obtain powdery crystals (2.66 g) of compound (1D). The yield was 57.8%.

The $^1$H-NMR spectrum (solvent: CDCl$_3$, internal standard: TMS) of compound (1D) was such that δ (ppm): 0.89 to 1.28 (18H, m), 1.69 to 1.92 (8H, m), 2.30 (2H, m), 2.65 (1H, m), 6.12 (1H, d), 6.48 (1H, m), 6.73 (1H, d), 7.26 (2H, m), 7.54 (2H, m), 7.87 (2H, m).

Figure 10:
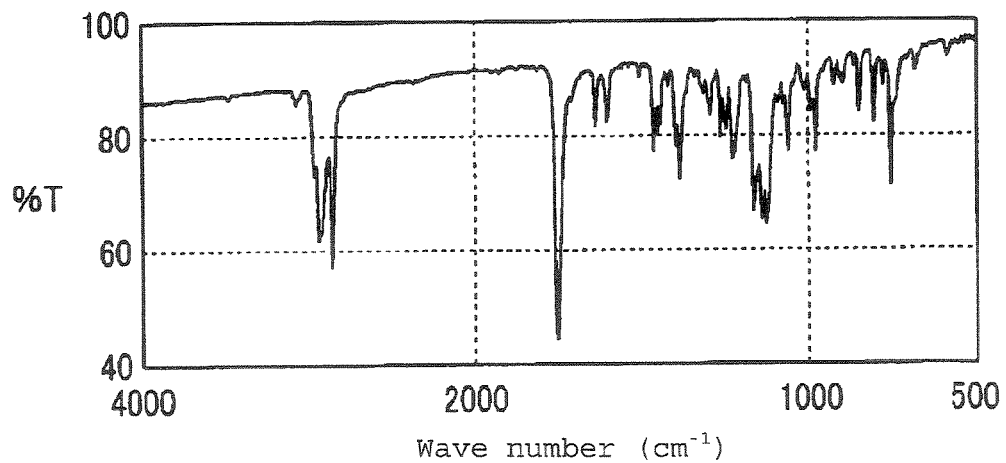
FIG. 10 is an infrared absorption spectrum of compound (1D).

As a result of observation of compound (1D) by a polarizing microscope, it underwent phase transition from crystals to a nematic phase at 118° C. when the temperature was increased, and accordingly it was confirmed to have liquid crystallinity. The phase transition temperature to an isotropic phase could not be confirmed due to thermal polymerization. The infrared absorption spectrum (KBr disk) of compound (1D) is shown in FIG. 10.

Example 10

Preparation of Compound (1W)

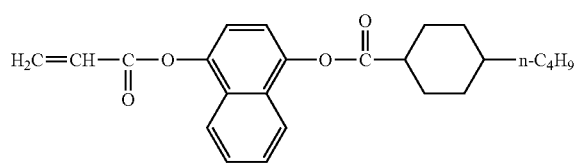

(1W)

Compound (1W) (1.5 g) was obtained in the same manner as in Example 9-2 except that trans-4-(trans-4-n-butylcyclohexyl)cyclohexanecarboxylic acid was changed to trans-4-n-butylcyclohexanecarboxylic acid (2.02 g, 0.011 mol). The yield was 39.5%.

The $^1$H-NMR spectrum (solvent: CDCl$_3$, internal standard: TMS) of compound (1W) was such that δ (ppm): 0.91 (3H, t), 1.07 (2H, m), 1.30 (7H, m), 1.68 (2H, m), 1.93 (2H, m), 2.27 (2H, m), 2.67 (1H, m), 6.11 (1H, d), 6.47 (1H, m), 6.72 (1H, d), 7.25 (2H, m), 7.53 (2H, m), 7.87 (2H, m).

Figure 11:
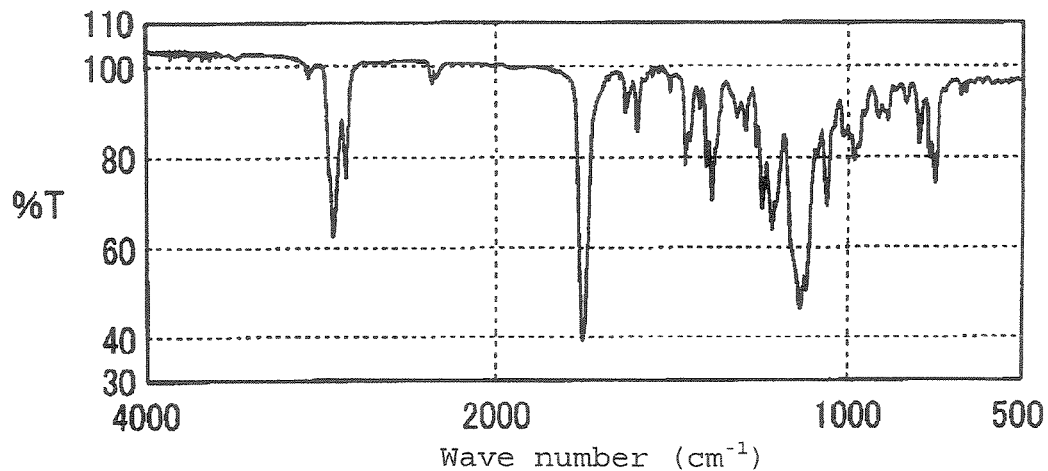
FIG. 11 is an infrared absorption spectrum of compound (1W).

As a result of observation of compound (1W) by a polarizing microscope, its phase changed from crystals to an isotropic liquid at 88° C. when the temperature was increased. The infrared absorption spectrum (KBr disk) of compound (1W) is shown in FIG. 11.

Example 11

Example (3) for Preparation of Phase Plate

Compounds (1D) and (1W) obtained in Examples 9 and 10 were mixed in a ratio of 5:5 (molar ratio) to obtain liquid crystal composition C. Then, a photopolymerization initiator (tradename: Irgacure907, manufactured by Ciba Specialty Chemicals) was added to liquid crystal composition C in an amount of 0.5 mass % based on liquid crystal composition C to obtain liquid crystal composition C1. Using liquid crystal composition C1, a phase plate C was prepared in the same manner as in Example 7.

Figure 12:
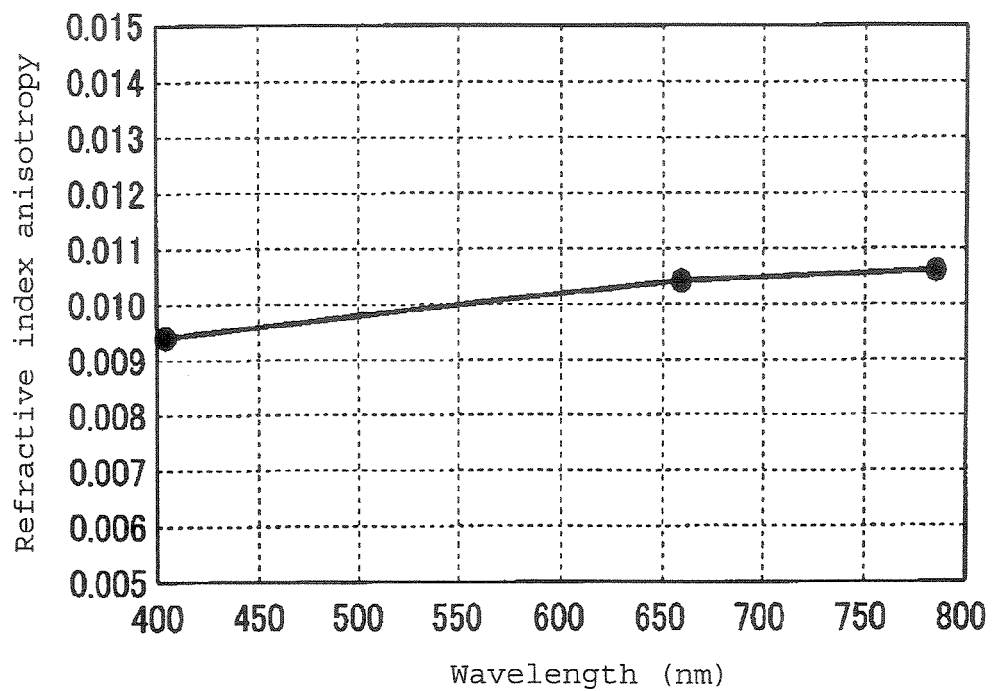
FIG. 12 is a graph illustrating the wavelength dependence of the refractive index anisotropy of a phase plate C obtained in Example 11.

Regarding the phase plate C, phase differences at wavelengths of 405 nm, 660 nm and 785 nm were measured. The phase difference values were divided by the thickness of the phase plate C (the thickness of the optical anisotropic material after polymerization) to calculate the value of the refractive index anisotropy at each wavelength. The result is shown in FIG. 12. It was confirmed that the value of the refractive index anisotropy of the phase plate C increases as the wavelength of light increases.

INDUSTRIAL APPLICABILITY

The polymerizable compound of the present invention is useful for adjustment of the wavelength dispersion properties of the refractive index anisotropy. Therefore, an optical anisotropic material obtained by polymerizing a polymerizable liquid crystal composition containing the polymerizable compound is useful as an optical element such as a phase plate and a polarizing diffraction element. By properly adjusting the wavelength dispersion, such an optical element can be utilized as a broadband wave plate or a polarizing diffraction element of which the efficiency is independent of the wavelength, and is thereby useful as an optical element to be used for an optical head device using laser beams at a plurality of wavelengths, the demand for which is increasing in recent years.

The entire disclosures of Japanese Patent Application No. 2005-115886 filed on Apr. 13, 2005 and Japanese Patent Application No. 2005-362891 filed on Dec. 16, 2005 including specifications, claims, drawings and summaries are incorporated herein by reference in their entireties.

What is claimed is:

1. A polymerizable liquid crystal composition containing a polymerizable compound having a mesogen structure comprising the following condensed benzene ring group (A) and the following 6-membered cyclic group (B) bonded to at least one bond in the group (A) directly or via a connecting group —OCO— or —COO—, and a monovalent terminal group bonded to each of both terminals of the mesogen structure, at least one of the terminal groups being a monovalent organic group having a polymerizable moiety, where the condensed benzene ring group (A) is a naphthalenediyl group having bonds at 1-position and at 4- or 5-position, or an anthracenediyl group having bonds at 1- or 9-position and at 4-, 5- or 10-position; and the 6-membered cyclic group (B) is a 1,4-phenylene group, a trans-1,4-cyclohexylene group or a bivalent group having at least two groups selected from these groups bonded directly or via a connecting group, wherein the polymerizable compound is represented by the following formula (1):

$$CH_2=CR^1—COO-J^1-(E^1-J^2)_n-W^1-J^3-M-R^2 \qquad (1)$$

where $R^1$, $R^2$, n, $J^1$, $J^2$, $J^3$, $E^1$, $W^1$ and M are as follows:

$R^1$: a hydrogen atom or a methyl group, $R^2$: a $C_{2-8}$ alkyl group, n: 0 or 1, $J^1$: a single bond, —$(CH_2)_a$— or —$(CH_2)_bO$— (wherein each of "a" and "b" which are independent of each other, is an integer of from 2 to 8), $J^2$, $J^3$: each independently a single bond, —OCO— or —COO—, $E^1$: a 1,4-phenylene group or a trans-1,4-cyclohexylene group, provided that a hydrogen atom in such a group may be substituted by a chlorine atom, a fluorine atom, a methyl group or a cyano group, $W^1$: a naphthalene-1,4-diyl group, a naphthalene-1,5-diyl group, an anthracene-1,4-diyl group, an anthracene-1,5-diyl group, an anthracene-1,10-diyl group, an anthracene-4,9-diyl group, an anthracene-5,9-diyl group or an anthracene-9,10-diyl group, provided that a hydrogen atom in such a group may be substituted by a chlorine atom, a fluorine atom, a methyl group or a cyano group, and M: a group selected from groups represented by the following formulae (a) to (f):

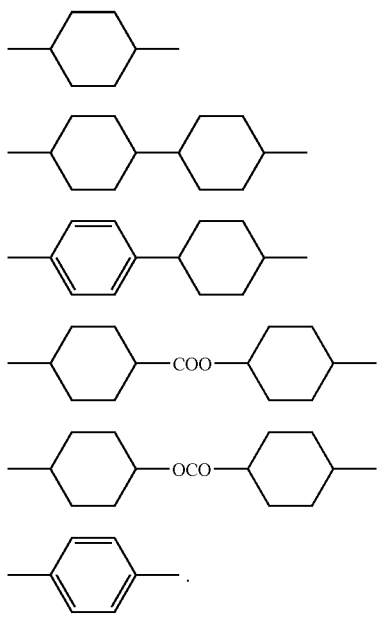

2. The polymerizable liquid crystal composition according to claim 1, wherein M is a group selected from groups represented by the following formulae (a) to (e):

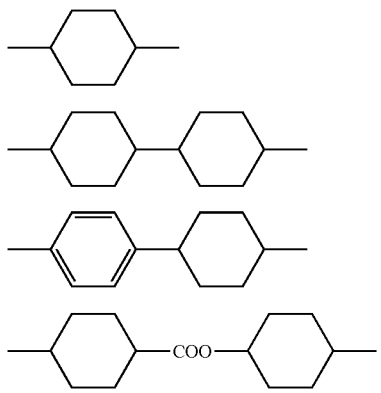

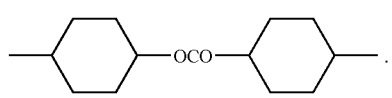

3. The polymerizable liquid crystal composition according to claim 2, wherein M is a trans-1,4-cyclohexylene group or a trans,trans-4,4'-bicyclohexylene group.

4. The polymerizable liquid crystal composition according to claim 1, which further contains a polymerizable compound represented by the following formula (2):

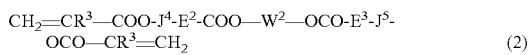

wherein $R^3$, $J^4$, $J^5$, $E^2$, $E^3$, and $W^2$ are as follows:

$R^3$: a hydrogen atom or a methyl group, $J^4$: —$(CH_2)_tO$— or —$(CH_2)_uO$—CO— (wherein each of "t" and "u" which are independent of each other, is an integer of from 2 to 6), $J^5$: —$O(CH_2)_c$— or —COO—$(CH_2)_d$— (wherein each of "c" and "d" which are independent of each other, is an integer of from 2 to 6)

$E^2$, $E^3$: each independently a 1,4-phenylene group or a trans-1,4-cyclohexylene group, provided that a hydrogen atom in such a group may be substituted by a chlorine atom, a fluorine atom, a methyl group or a cyano group, and $W^2$: a naphthalene-1,4-diyl group, a naphthalene-1,5-diyl group, an anthracene-1,4-diyl group, an anthracene-1,5-diyl group, an anthracene-1,10-diyl group, an anthracene-4,9-diyl group, an anthracene-5,9-diyl group or an anthracene-9,10-diyl group, provided that a hydrogen atom in such a group may be substituted by a chlorine atom, a fluorine atom, a methyl group or a cyano group.

5. The polymerizable liquid crystal composition according to claim 1, wherein the content of the polymerizable compound represented by the formula (1) is at least 10 mass % based on the polymerizable liquid crystal composition.

6. An optical anisotropic material comprising a polymerized composition of claim 1 the polymerizable liquid crystal composition as defined in claim 1.

7. The optical anisotropic material according to claim 6, which is optically uniaxial and of which the value of refractive index anisotropy Δn which is a difference between the ordinary refractive index $n_o$ and the extraordinary refractive index $n_e$ increases as the wavelength of light to be used increases.

8. An optical element to control polarization state and/or phase state of light to be used, comprising the optical anisotropic material as defined in claim 6.

9. A phase plate, comprising the optical anisotropic material as defined in claim 6.

10. A polarizing diffraction element having a diffraction grating region to diffract incident light, wherein the diffraction grating region comprises a first member made of a first material and a second member made of a second material, the first member and the second member differ from each other in the refractive index to at least one polarized light, and the first member and the second member are disposed alternately to be in contact with each other; and the first material is the optical anisotropic material as defined in claim 6.

11. An optical head device comprising a semiconductor laser, an objective lens and a photodetector, and a phase plate and/or a polarizing diffraction element disposed between the objective lens and the photodetector, wherein the phase plate is the phase plate as defined in claim 9.

12. An optical head device comprising a semiconductor laser, an objective lens and a photodetector, and a phase plate and/or a polarizing diffraction element disposed between the objective lens and the photodetector, wherein the polarizing diffraction element is the polarizing diffraction element as defined in claim 10.

13. A polymerizable compound represented by the following formula (1):

$$CH_2=CR^1-COO-J^1-(E^1-J^2)_n-W^1-J^3-M-R^2 \qquad (1)$$

wherein $R^1$, $R^2$, n, $J^1$, $J^2$, $J^3$, $E^1$, $W^1$ and M are as follows:
- $R^1$: a hydrogen atom or a methyl group,
- $R^2$: a $C_{2-8}$ alkyl group,
- n: 0 or 1,
- $J^1$: a single bond, $-(CH_2)_a-$ or $-(CH_2)_bO-$ (wherein each of "a" and "b" which are independent of each other, is an integer of from 2 to 8),
- $J^2$, $J^3$: each independently a single bond, —OCO— or —COO—,
- $E^1$: a 1,4-phenylene group or a trans-1,4-cyclohexylene group, provided that a hydrogen atom in such a group may be substituted by a chlorine atom, a fluorine atom, a methyl group or a cyano group,
- $W^1$: a naphthalene-1,4-diyl group, a naphthalene-1,5-diyl group, an anthracene-1,4-diyl group, an anthracene-1,5-diyl group, an anthracene-1,10-diyl group, an anthracene-4,9-diyl group, an anthracene-5,9-diyl group or an anthracene-9,10-diyl group, provided that a hydrogen atom in such a group may be substituted by a chlorine atom, a fluorine atom, a methyl group or a cyano group, and
- M: a group selected from groups represented by the following formulae (a) to (f):

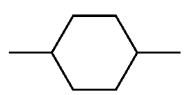
(a)

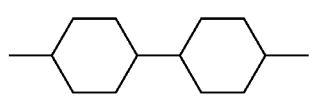
(b)

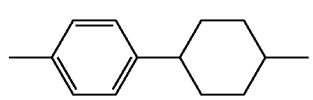
(c)

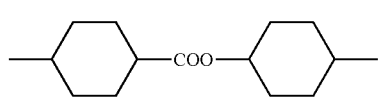
(d)

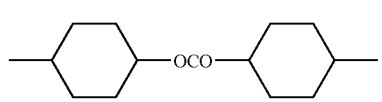
(e)

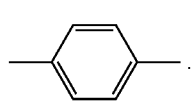
(f)

14. The polymerizable liquid crystal composition according to claim 4, wherein a sum of the content of the polymerizable compound represented by the formula (1) and the content of the polymerizable compound represented by the formula (2) is at least 10 mass % based on the polymerizable liquid crystal composition.

\* \* \* \* \*